United States Patent
Willis et al.

(10) Patent No.: US 11,278,493 B2
(45) Date of Patent: Mar. 22, 2022

(54) OPHTHALMIC FORMULATIONS PROVIDING DURABLE OCULAR LUBRICATION

(71) Applicant: EternaTear, Inc., Raleigh, NC (US)

(72) Inventors: Timothy R. Willis, Raleigh, NC (US); Ralph P. Stone, Fort Worth, TX (US)

(73) Assignee: ETERNATEAR, INC., Raleigh, NC (US)

( * ) Notice: Subject to any disclaimer, the term of this patent is extended or adjusted under 35 U.S.C. 154(b) by 0 days.

(21) Appl. No.: 16/708,120

(22) Filed: Dec. 9, 2019

(65) Prior Publication Data

US 2020/0179281 A1 Jun. 11, 2020

Related U.S. Application Data

(60) Provisional application No. 62/777,588, filed on Dec. 10, 2018.

(51) Int. Cl.
| | |
|---|---|
| *A61K 9/107* | (2006.01) |
| *A61K 9/00* | (2006.01) |
| *A61K 35/644* | (2015.01) |
| *A61K 47/44* | (2017.01) |

(52) U.S. Cl.
CPC ............ *A61K 9/107* (2013.01); *A61K 9/0048* (2013.01); *A61K 35/644* (2013.01); *A61K 47/44* (2013.01)

(58) Field of Classification Search
CPC .... A61K 9/107; A61K 9/0048; A61K 35/644; A61K 47/44; A61K 9/1075; A61K 47/14
See application file for complete search history.

(56) References Cited

U.S. PATENT DOCUMENTS

| | | |
|---|---|---|
| 4,151,001 A | 4/1979 | Anderson et al. |
| 4,421,748 A | 12/1983 | Trager et al. |
| 4,914,088 A | 4/1990 | Glonek et al. |
| 5,252,246 A | 10/1993 | Ding |
| 5,278,151 A | 1/1994 | Korb et al. |
| 5,294,607 A | 3/1994 | Glonek et al. |

(Continued)

FOREIGN PATENT DOCUMENTS

| | | |
|---|---|---|
| EP | 0 459 148 A2 | 12/1991 |
| EP | 0 535 545 | * 7/1993 |

(Continued)

OTHER PUBLICATIONS

Wikipedia Contributors, "Beeswax," Wikipedia, accessed Sep. 27, 2018. Available at https://en.wikipedia.org/w/index.php?title=Beeswax&oldid=861444220, 7 pages.

(Continued)

*Primary Examiner* — Gollamudi S Kishore
(74) *Attorney, Agent, or Firm* — Barnes & Thornburg LLP

(57) ABSTRACT

This disclosure is directed to an ophthalmic formulation for dry eye and other ocular indications that provides long-lasting benefits. The formulations described herein provide durable relief and last two to ten longer on the eye than currently marketed products. The disclosure also provides methods of alleviating the symptoms of dry eye, methods for delivering ophthalmic pharmaceuticals, and methods of manufacture of the long-lasting ophthalmic formulations.

7 Claims, 8 Drawing Sheets

(56) References Cited

U.S. PATENT DOCUMENTS

| | | | |
|---|---|---|---|
| 5,371,108 | A | 12/1994 | Korb et al. |
| 5,578,586 | A | 11/1996 | Glonek et al. |
| 5,672,358 | A | 9/1997 | Tabibi |
| 5,942,558 | A | 8/1999 | Korb et al. |
| 6,436,429 | B1 | 8/2002 | Peyman |
| 8,591,033 | B2 | 11/2013 | Korb et al. |
| 8,746,883 | B2 | 6/2014 | Korb et al. |
| 8,915,592 | B2 | 12/2014 | Korb et al. |
| 9,044,388 | B2 | 6/2015 | Korb et al. |
| 9,161,905 | B2 | 10/2015 | Korb et al. |
| 9,545,197 | B2 | 1/2017 | Korb et al. |
| 2010/0086512 | A1 | 4/2010 | Schaefer |
| 2010/0247593 | A1* | 9/2010 | Wikberg ............... A61K 31/366 424/422 |
| 2012/0128763 | A1* | 5/2012 | Maskin .................. A61K 35/60 424/450 |
| 2013/0216596 | A1* | 8/2013 | Viladot Petit ............ A61K 8/64 424/401 |
| 2014/0206764 | A1* | 7/2014 | Liu .......................... A61P 27/02 514/560 |
| 2015/0202306 | A1* | 7/2015 | Coffey .................. A61K 9/0048 514/772.6 |
| 2015/0297511 | A1* | 10/2015 | Xia ........................ A61K 47/34 424/725 |
| 2016/0199428 | A1 | 7/2016 | Simmons et al. |
| 2016/0338952 | A1* | 11/2016 | Ketelson ............. B01F 17/0085 |
| 2016/0354307 | A1* | 12/2016 | Hilliard ................ A61K 9/0051 |
| 2018/0008538 | A1* | 1/2018 | Izquierdo Torres .... A61P 27/02 |
| 2018/0325854 | A1* | 11/2018 | Coulon .................. A61P 27/02 |

FOREIGN PATENT DOCUMENTS

| | | | |
|---|---|---|---|
| WO | 2006004577 | A2 | 1/2006 |
| WO | 2015055301 | A1 | 4/2015 |
| WO | 2017074420 | A1 | 5/2017 |
| WO | 2017132190 | A1 | 8/2017 |

OTHER PUBLICATIONS

Wikipedia Contributors, "Eye Drop," Wikipedia, accessed Sep. 13, 2018. Available at https://en.wikipedia.org/w/index.php?title=Beeswax&oldid=847772327, 4 pages.

Wikipedia Contributors, "Surfactant," Wikipedia, accessed Sep. 13, 2018, 11:50 UTC. Available at https://en.wikipedia.org/w/index.php?title=Beeswax&oldid=858602819, 11 pages.

Freeman, P. David, and Kahook, Malik Y. "Preservatives in Topical Ophthalmic Medications: Historical and Clinical Perspectives." Expert Rev Ophthalmol. 2009:4(1):59-64. Expert Reviews Ltd., London.

Klier, John. "Microemulsions." In Kirk-Othmer Encyclopedia of Chemical Technology, John Wiley & Sons, Inc (Ed.), United States, dated Jul. 13, 2012, 22 pages.

Korb, Donald R. "Survey of Preferred Tests for Diagnosis of Tear Film and Dry Eye." Cornea, 19(4): 483-486 (2000), Lippincott Williams and Wilkins, Inc., Philadelphia.

Kostansek, Edward. "Emulsions." In Kirk-Othmer Encyclopedia of Chemical Technology, John Wiley & Sons, Inc (Ed.), United States, dated Jul. 12, 2012, 24 pages.

Lanigan, Rebecca S., and Yamarik, Torrill A. "Final Report on the Safety Assessment of PEG-6, -8, and -20 Sorbitan Beeswax." Int. J. Toxicology, 20(Supp. 4):27-38 (2001). Cosmetic Ingredient Review Panel, SAGE Publishing, United States.

Leray, Claude. "Waxes." In Kirk-Othmer encyclopedia of Chemical echnology John Wiley & Sons, Inc (Ed.), United States, dated Sep. 15, 2016, 25 pages.

Moshirfar, Majid et al. "Artificial tears potpourri: A literature review." Clinical Ophthalmology, vol. 2014 (8):1419-1433 (2014), Dove Press, United States.

Patel, Ashaben et al. "Ocular drug deliver systems: An overview." World J Pharmacol., 2(2): 47-64 (2013). Baishideng Publishing Group Inc, United States.

Pucker, AD, NG, SM, and Nichols, JJ. "Over the counter (OTC) artificial teardrops for dry eye syndrome," Cochrane Database of Systematic Reviews, Issue 2. Art, No. CD009729 (2016). John Wiley & Sons, Ltd., United States.

Restasis MultiDose TM [product prescribing information], Irvine, CA: Allergan: revised Oct. 2016.

Sweeney, Deborah F., et al. "Tear film stability: A review." Experimental Eye Research, 117, 28-38 (2013). Elsevier Ltd., United States.

Tadros, Tharwat. "Surfactants." In Kirk-Othmer Encyclopedia of Chemical Technology, John Wiley & Sons, Inc (Ed.), United States, dated Jul. 13, 2012, 46 pages.

International Search Report for PCT/US2019/065191, dated Mar. 19, 2020.

Fisher Chemical—Fisher Scientific, product listing for "Mineral Oil, Light (NF/FCC), Fisher Chemical", [online] https://www.fishersci.com/shop/products/mineral-oil-light-nf-fcc-fisher-chemical-3/O1211 (Accessed May 13, 2021).

Fisher Chemical—Fisher Scientific, product listing for "Mineral Oil, Heavy (USP/FCC), Fisher Chemical", [online] https://www.fishersci.com/shop/products/mineral-oil-light-nf-fcc-fisher-chemical-2/O1211 (Accessed May 13, 2021).

* cited by examiner

OPHTHALMIC FORMULATIONS PROVIDING DURABLE OCULAR LUBRICATION

CROSS REFERENCE TO RELATED APPLICATIONS

This application claims the benefit of U.S. Provisional Application 62/777,588 filed Dec. 10, 2018, inventors Timothy Willis and Ralph Stone, entitled "OPHTHALMIC FORMULATIONS PROVIDING LONG-LASTING EYE LUBRICATION" which is hereby incorporated by reference in its entirety

1. FIELD

The present disclosure provides a novel long-lasting ophthalmic formulation for ocular therapy for dry eye and other ocular indications. The formulation described herein provides relief for dry eye that lasts two to ten times longer on the eye than currently marketed products. Methods of treatment, methods of delivery of pharmaceuticals, and methods of preparation are also provided.

2. BACKGROUND

2.1. Introduction

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly admitted or impliedly admitted as prior art against the present disclosure.

Dry eye is an ophthalmic medical condition which is currently exhibited in over 320 million patients worldwide and over 15% of the US population. The discomfort resulting from a dry eye condition may include ocular dryness, grittiness, burning, soreness, scratching, or foreign body reaction. The degree of discomfort is dependent upon the subject and the condition of the subject. Proposed causes for dry eye, treatment, and symptoms are described in a compendium of papers edited by Holly, The Preocular Tear Film in Health, Disease, and Contact Lens Wear, The Dry Eye Institute, Lubbock, Tex. 1986; edited by David A. Sullivan, Lacrimal Gland, Tear Film, and Dry Eye Syndromes, 1994, Plenum Press, New York; edited by David A. Sullivan et. al, Lacrimal Gland, Tear Film, and Dry Eye Syndromes 2, 1998, Plenum Press, New York; edited by David A. Sullivan et. al, Lacrimal Gland, Tear Film, and Dry Eye Syndromes 3, Part A and B, 2002, Kluwer Academic/Plenum Publishers, New York, The 2007 DEWS Report Ocular Surface July 2007, The DEWS II Report Ocular Surface July 2017 incorporated herein by reference for their teachings of the dry eye condition and the treatment thereof.

In addition, for many patients the symptoms associated with dry eye are often exacerbated by use ocular prostheses such as contact lenses. In some cases, individuals will stop wearing contact lenses due, either solely or in part, to dry eye and its symptoms. Further, the rate of evaporation from the eye is accelerated by the nature of the contact lens material and surface. The physical presence of the contact lens results in menisci formation with additional physical and evaporative effects, even with subjects having an adequate tear film. For many subjects, contact lens intolerance is not overcome by topical application of tear substitutes. Therefore, there is a need for improved compositions and processes for treatment of the dry eye condition and for improving tolerance to ocular prostheses. Moreover, the patient may present with ocular signs including lid wiper epitheliopathy and corneal staining either when experiencing dry eye or when wearing an ocular prostheses.

The most common treatment for dry eye involves temporary alleviation of dry eye symptoms by topical application of an artificial tear substitute that provide a volume of liquid to the surface of the eye and neighboring tissues, e.g., eyelids, cornea. Typical commercially available tear substitute compositions comprise water soluble polymer solutions. These water soluble polymer solutions only provide limited relief due to an average on eye dwell time being less than 15 minutes. Examples of such solutions include saline solutions of polyvinyl alcohol, hydroxypropylmethyl cellulose, or carboxymethyl cellulose. U.S. Pat. No. 4,421,748 teaches an artificial tear composition comprising an aqueous hypotonic solution of lecithin and a viscosity-adjusting agent such as a solution of a soluble cellulose. An aqueous tear film extends over the ocular surface and maintains a moist and lubricated ocular surface. It is also known that dehydration of moisture from the eye may result in discomfort. Further, compositions are available in the market intended for dry eye treatment. Commercially available compositions are primarily aqueous materials that supplement the tear film by adding a film of a water soluble polymer over the surface of the eye. These films are short lived and provide limited relief.

A number of improved compositions for dry eye treatment are disclosed in U.S. Pat. Nos. 4,914,088; 5,278,151; 5,294,607; 5,578,586, and 9,161,905, each incorporated herein by reference for its teaching of how to form an oil film over the surface of the eye including compositions and uses. U.S. Pat. No. 4,914,088 teaches the use of certain charged phospholipids for the treatment of dry eye symptoms. The addition of a charged phospholipid to the eye is believed to assist in replicating the tear film that would naturally occur in the eye. In accordance with the patent, the phospholipid composition, preferably in the form of an aqueous emulsion, is topically applied to the eye where it is believed to disperse over the ocular surface and form a film that replicates a lipid layer that would be formed by the spreading of a naturally occurring lipid secreted principally from the Meibomian glands during blinking. Because the phospholipid, when applied to the eye carries a net negative charge, it is believed that aligned molecules repel each other preventing complex aggregate formation thereby resulting in a stable phospholipid film. The patent theorizes that the film formed from the charged phospholipid assists in the formation of a barrier film reducing evaporation of the aqueous layer, thereby preserving the tear film. Others have theorized that the phospholipid also functioned as a surfactant maintaining the emulsion stability.

The above referenced U.S. Pat. Nos. 5,278,151; 5,294,607; 5,578,586; 9,279,095; and 9,375,401 disclose additional improvements in dry eye treatment. In these patents, the dry eye treatment composition of U.S. Pat. No. 4,914,088 is improved by the addition of an oil to the eye treatment composition, preferably a non-polar oil such as mineral oil comprised of hydrocarbon ingredients. The oil is added to improve the performance of a dry eye treatment composition by increasing the longevity of the tear film formed on the eye as a consequence of the formation of an oil film over the ocular surface that functions as an evaporation barrier—i.e., by providing and/or thickening the dehydration barrier (the oil layer) on the outer surface of the tear film. Thus, the oil increases the efficacy of the dry eye treatment solution and reduces performance variability from subject to subject. It also supplements the oils provided from the Meibomian gland which in many cases of dry eye does not provide sufficient oils to provide an adequate lipid tear layer. A preferred embodiment disclosed in the above referenced patents is a dry eye treatment composition comprising a meta stable oil-in-water emulsion where the water phase includes the charged phospholipid believed to function both as an emulsifier and as a surfactant that assists in spreading of the oil over the eye to form a non-blurring film bonding of the oil to the aqueous layer of the tear film. The emulsion is desirably "meta" stable so that when the emulsion is applied to the eye, it will rapidly break and spread over the ocular surface when it first comes into contact with the ocular environment.

In the patent literature described above, meta stable emulsions were formulated whereby the total amount of oil added to the eye preferably does not exceed 25 μL, more preferably varies between about 1 and 10 μL and most preferably varies between about 1 and 5 μL. If the amount of oil added to the eye is in excess of 25 μL, the oil layer on the surface of the eye may be of excessive thickness resulting in formation of oil globules on the surface of the eye. These globules are likely to result in prolonged blurred vision. To achieve control of the amount of oil added to the eye, the concentration limits of the oil in the emulsion are controlled within reasonable limits. An emulsion containing the oil in a concentration of at least 0.1 percent by weight of the total composition provides some benefits, a preferred concentration is at least 1.0 percent of the weight of the treatment composition, and the most preferred oil content varies between about 2.5 and 12.5 percent by weight of the emulsion.

U.S. Pat. No. 5,371,108 teaches a method for creating a gel comprising oil and wax to form a tear film on the ocular surface and the presence of wax in the gel can prolong the residence time of oil. A wax-containing gel has not been produced and marketed commercially because of the difficulty in homogenizing the wax in such a way that does not induce visual blurring beyond what would be acceptable by most consumers. Specifically, autoclaving to sterilize the wax contain formulation leads to increased particle size which leads to irritation and blurred vision. Gels are semisolid formulations with low viscosity. In contrast, this disclosure is directed to metastable emulsions that behave as flowing liquids at room temperature. Emulsions behave as liquids and as such do not exhibit a static internal structure.

U.S. Pat. No. 5,278,151 teaches that an oil-in-water emulsion can contain a natural wax.

With regard to natural tears, Shimizu and coworkers have reported a typical tear volume is 12.4±6.2 μL. Shimizu et al., 1993 Nippon Ganka Gakkai Zasshi. 97(9): 1047-52. Others have reported small volumes, 6.2±2.0 μL. Mishima et al., 1996, IOVS 1966; 5: 264-76.

Current commercially available products, including oil and water emulsion products, often supplement one or more layers of the tear film through various combinations of oils, aqueous solutions, and mucomimetics. These lipid emulsions provide sufficient lubrication and prevention against desiccation, but they remain inadequate in terms of their ability to remain on the eye and provide lasting relief, which is the most desired clinical result. However, these compositions fail to bind the interstitial layers, causing those layers to lose their natural stability on the surface of the eye and thus have limited relief due to their on eye dwell time being less than 45 minutes. Without connectivity to each subsequent layer of the film, the lipid, aqueous, and mucin layers, whether natural, artificial or some combination thereof, tend to be expressed in a period of time too short to provide lasting comfort from the symptoms of dry eye. See FIG. 1 for an enlarged view of the eye and the components of the layers and interfaces of the tear film. The normal tear film is 3-6 μM thick. The two insets with lines to the tear film show enlarged views of the lipid/aqueous interface and the aqueous/mucin interface. The third inset shows the thinning of the layers and interfaces associated with dry eye. In particular, it shows the thinning of (i) the aqueous layer, (ii) the unbound mucin layer, and (iii) the bound mucin layer on the surface of the corneal epithelial cells. Existing products do not stabilize, the different layers and interfaces of the tear film including the lipid layer. Thus, the existing products do not create a stable lipid layer and provide long term benefits.

Methods used to quantify the effectiveness of tear substitutes for dry eye treatment solutions have historically not been standardized, and many methods used to quantify the results obtained using such tear substitute compositions are often inaccurate. For this reason, reported relief of dry eye symptoms using known tear substitutes varies considerably from subject to subject, and regardless of the method used to quantify relief using a tear substitute, relief often does not exceed several minutes.

For a therapy to provide lasting relief, it would have to supplement not only the deficient layers of the tear film, but also have the chemical and binding properties necessary to promote homeostasis of those layers on the ocular surface. For any solution to be viable for a large number of patients with symptoms that vary greatly in cause and magnitude, the therapy would need to mimic as closely as possible the properties of the natural human tear film. Though research has reported the presence of waxes within the tear film, their purpose has not been well-understood.

Because the purpose of the tear film is to protect the ocular surface and provide lubrication to the ocular surface as well as can be used to provide ocular delivery of active pharmaceutical ingredients (API) in small concentrations has been a challenge to industry. See Patel et al. 2013, "Ocular drug delivery systems: An overview" *World J. Pharmacol* 2(2) 47-64. For an excipient to be a good carrier of active pharmaceutical ingredients (APIs) it needs to mimic the properties and osmolarity of the natural tear film and remain on the eye for an extended period of time. Such a product would increase the bioavailability of the API to the corneal epithelial cells, a long desired pathway for ocular drugs.

3. SUMMARY OF THE DISCLOSURE

Disclosed herein is an oil-in-water emulsion with the inclusion of natural or synthetic wax esters or suitable combination of wax esters in the tear film which rebuilds the tear film in a several ways. In particular it rebuilds the tear film by increasing the integrity of the interstitial layers themselves, binds mucin to aqueous and or the corneal cells and aqueous to lipid as well as builds and thickens the mucin, aqueous and lipid layers themselves. The binding and thickening process and subsequent homeostasis enabled by the wax esters and their hydrolysis products allows the layers of the tear film to cling to each other, thus mimicking the natural tear film and providing a tear film that remains on the eye for extended periods of time. This vehicle mimics the tear film as well as providing a vehicle to be used for pharmaceutical drug delivery as noted herein.

In one embodiment, this disclosure provides an ophthalmic solution which comprises an oil-in-water emulsion comprising water; an oil; a surfactant; a wax ester, which may be a beeswax or suitable combination of wax esters; and wherein the ophthalmic solution (i) forms a meta stable emulsion which separates into an oil phase and a water phase on contact with an eye; and (ii) provides lubrication for about 2 to about 12 hours on the eye. In some embodiments, the ophthalmic solution provides lubrication for about 2 to about 5 hours on the eye. In other embodiments, the ophthalmic solution provides lubrication for about 2 to about 8 hours or 1 to 10 hours on the eye. Alternatively, it may provide greater than 3 hours of lubrication, greater than 5 hours, greater than 8 hours, or greater than 10 hours of lubrication on the eye.

An ophthalmic solution which comprises an oil-in-water emulsion comprising water; an oil; a surfactant; a wax ester such as beeswax comprising wax esters and other wax ester compositions in addition to partial hydrolysis products of theses esters; wherein the wax ester composition in the ophthalmic solution interacts with a mucin layer, an aqueous layer, and a lipid layer in an eye of a subject and act to maintain the integrity of an interstitial layer between the mucin layer and the aqueous layer, an interstitial layer between the aqueous layer and the lipid layer.

An ophthalmic solution which comprises a metastable emulsion comprising water; an lipid; a surfactant; an anti-inflammatory ingredient such as deactivated brewer's yeast or derivative such as ADP Ribose, wax esters and other wax ester compositions in addition to partial hydrolysis products of theses esters; wherein wax ester composition in the ophthalmic solution binding a mucin layer, an aqueous layer, and a lipid layer in an eye of a subject and act to maintain the integrity of an interstitial layer between the mucin layer and the aqueous layer, an interstitial layer between the aqueous layer and the lipid layer while enhancing the tear film and reducing ocular inflammation caused by dry eye.

In another embodiment, this disclosure provides an ophthalmic solution which comprises an lipid and wax based emulsion comprising water; an oil and wax or wax esters ingredient such as whale or seal oil or synthetic version ingredients thereof; a surfactant; and other wax ester compositions in addition to partial hydrolysis products of theses esters; wherein wax ester composition in the ophthalmic solution binding the mucin layer, the aqueous layer, and the lipid layer in an eye of a subject and act to enhance and maintain the integrity of an interstitial layer between the mucin layer and the aqueous layer, an interstitial layer between the aqueous layer and the lipid layer.

In another embodiment, this disclosure provides a method for alleviating the symptoms of dry eye which comprises contacting an eye with an ophthalmic solution comprising an oil-in-water emulsion which emulsion comprises: water; an oil; a surfactant; a wax ester such as beeswax and the products of partial hydrolysis; and wherein the ophthalmic solution (i) forms a meta stable emulsion which separates into an oil phase and a water phase on contact with an eye; and (ii) provides lubrication for about 2 to about 12 hours on the eye. In some embodiments, the method provides lubrication for about 2 to about 5 hours on the eye. In other embodiments, the method provides lubrication for about 2 to about 8 hours or 1 to 10 hours on the eye. Alternatively, the method may provide greater than 3 hours of lubrication, greater than 5 hours, greater than 8 hours, or greater than 10 hours of lubrication on the eye.

In another embodiment, this disclosure provides the method of preparing an ophthalmic solution providing lubrication for about 2 to about 12 hours on the eye, wherein the solution is a meta stable oil-in-water emulsion, wherein the method comprises: preparation of a wax ester dispersion comprising a wax ester such as a beeswax and a surfactant in a deionized water solution; preparation of an oil-in-water emulsion comprising an oil in a deionized water solution; separately autoclaving the beeswax dispersion and the oil-in-water emulsion under appropriate conditions; and aseptically blending the autoclaved wax ester dispersion and the oil-in-water emulsion so as to prepare the meta stable oil-in-water emulsion ophthalmic solution which provides lubrication for about 2 to about 12 hours on the eye. In a preferred embodiment, the lipid fraction is a homogenous oil-beeswax emulsified droplet. In one embodiment, the composition is used to deliver an over-the-counter or a prescription (generic or proprietary) medication.

4. BRIEF DESCRIPTION OF THE FIGURES

FIG. 1 shows an enlarged view of the tear film with the different regions. The normal tear film is 3-6 microns thick. The figure shows the lipid layer, the lipid/aqueous interface, the aqueous layer, the aqueous/mucin interface, the mucin layer, and the cornea. Two of the insets show enlarged views of the lipid/aqueous interface and the aqueous/mucin interface. The third inset shows the thinning of the layers and interfaces associated with dry eye. In particular, the third inset shows the thinning of (i) the aqueous layer, (ii) the unbound mucin layer, and (iii) the bound mucin layer which is bound the surface of the corneal epithelial cells.

Figure 5:
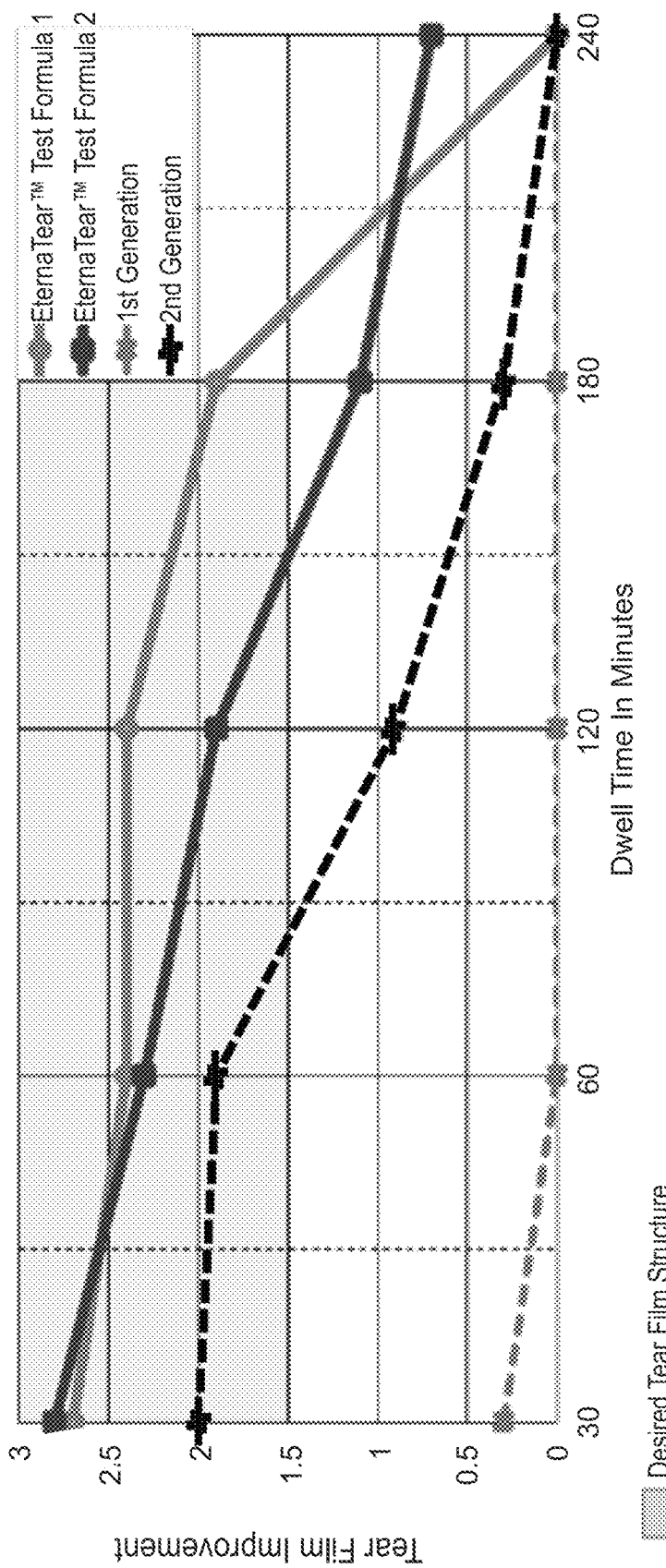

FIG. 5 shows a graph showing some of the comparative data for the dwell time in minutes and tear film score for 1% wax ester prototype product vs several commercially available solutions. The gray solid lines are two experiments with the EternaTear™ prototype 1% wax ester product, the gray dashed line is a first generation commercially available eye product. The black dashed line is a second generation commercially available eye product.

Figure 6:
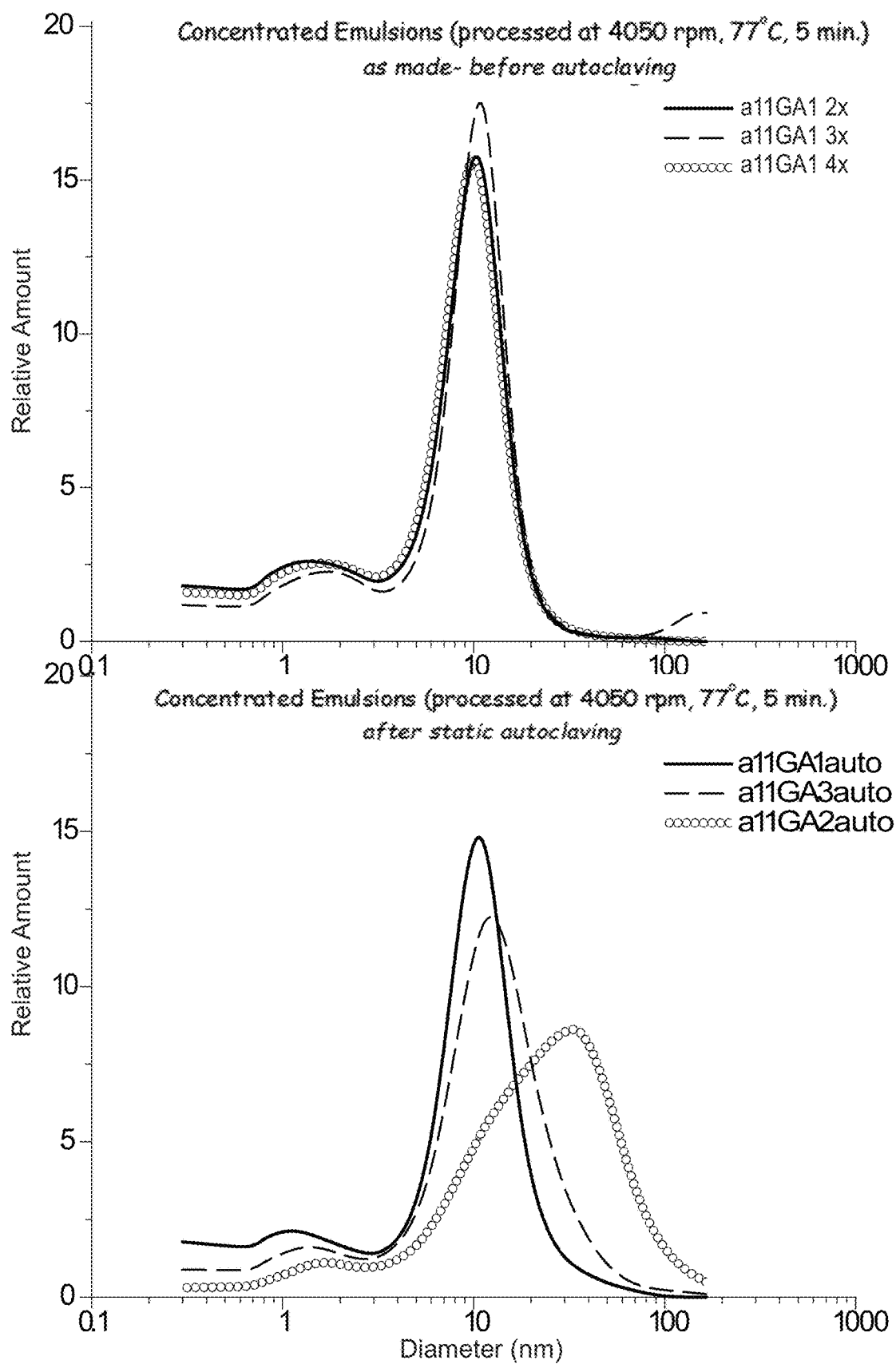

FIG. 6 shows the change in emulsion particle size distribution after autoclaving a 2× (solid line), 3× (dashed line), and 4× (open circles) concentrated emulsion. The top panel shows the particle size distribution for the 'as made' product, while the bottom panel shows the effect of autoclaving these samples.

Figure 7:
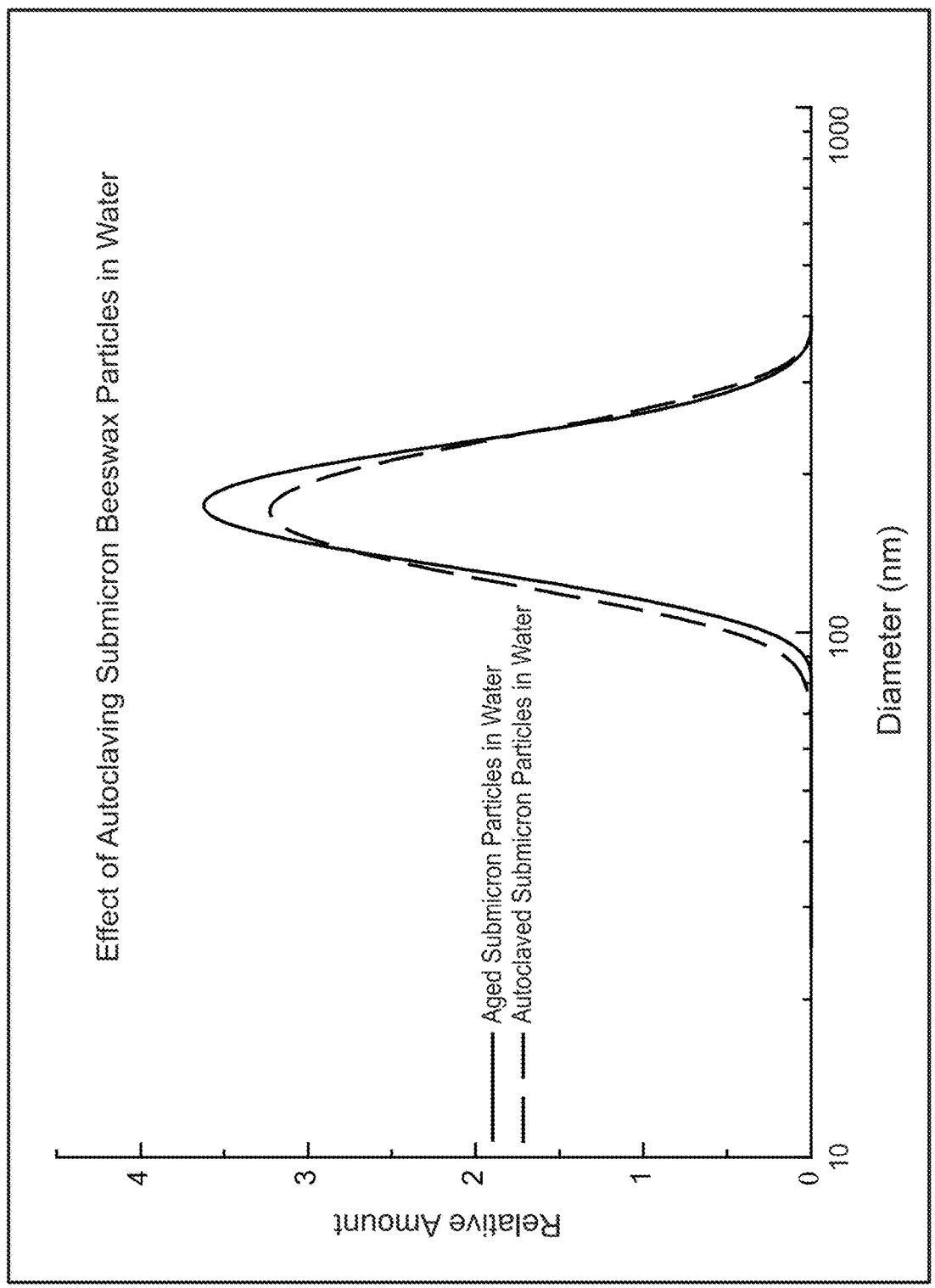

FIG. 7 shows particle size distributions of submicron wax ester particles before (solid black line) and after (dashed line) autoclaving.

Figure 8:
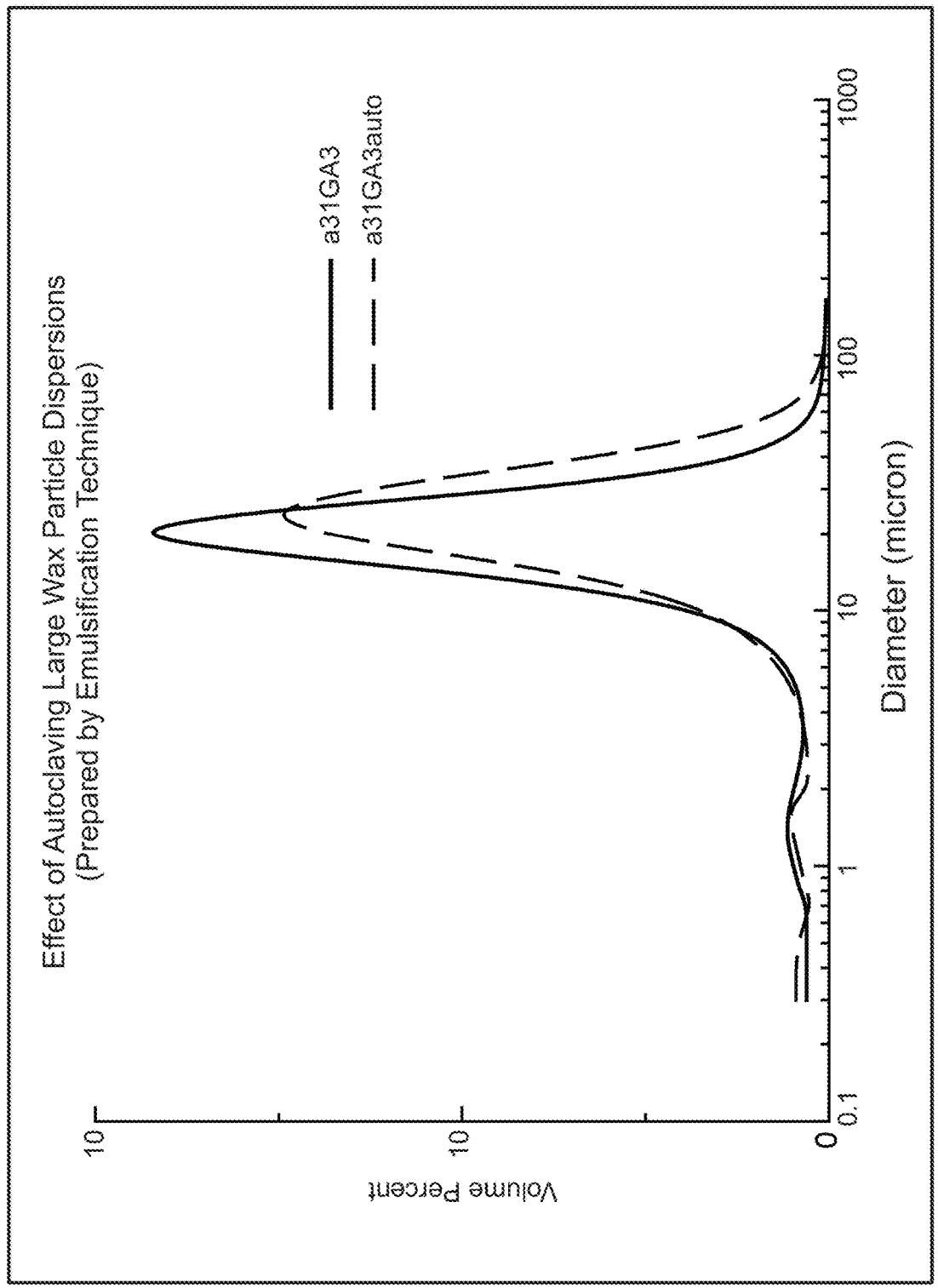

FIG. 8 shows the particle size distributions for wax ester particles obtained in the emulsification process in water with Octoxynol-40. The solid black line is for the sample as made, while the dashed line is the resulting distribution after autoclaving.

5. DETAILED DESCRIPTION OF THE DISCLOSURE

This invention relates to an emulsion composition for the formation of an artificial tear film over the ocular surface of the eye capable of providing enhanced ocular lubrication while reducing evaporation and remaining on the eye two to ten times longer than products currently available. The composition is also useful for delivering medication to the ocular surface and for treating individuals wearing ocular prostheses such as contact lenses as the composition wets and provides lubrication for both the ocular surface and the surface of the prosthesis. More particularly, the invention relates to emulsion compositions capable of augmenting and maintaining a stable tear film over the ocular surface for a period of time between two and six hours and/or delivering a medication to the eye without causing substantial blurring of vision nor discomfort. The emulsion is desirably in the form of an emulsion and is characterized by the use of wax or wax esters in combination with oils and appropriate surfactants and interstitial ingredients to increase dwell time on the ocular surface while providing a combination suitable for formation such an emulsion and maintaining the integrity of the emulsion during autoclaving.

In some embodiments the invention is an oil-in-water emulsion with natural wax esters such as beeswax dissolved in such a way that it can be delivered in a controlled manner and that its presence in an artificial tear film composition leads to dramatically increased dwell time on the eye by specifying the composition, concentration, and particle size of the wax ester in the meta stable oil-in-water emulsion. This wax-containing emulsion may use one or more surfactants to achieve the meta-stable properties one skilled in the art would accept as desirable for manufacture, storage, and application to the ocular surface. Further, one or both of these surfactants may be an anionic polar phospholipid.

The addition of natural or synthetic wax esters and their partial hydrolysis products, such as beeswax and its normal distribution throughout the various phases of the emulsion has the effect of improving the efficacy of the composition by allowing the lubricating elements to remain on the eye for a period of greater than one and up to twelve hours under normal conditions.

The chemical makeup of the invention and the manufacturing process by which that makeup is achieved replicates not only the discrete layers of the tear film by use of lipids, aqueous solutions and a mucomimetic, but also supplements its interstitial binding properties and builds and thickens the tear film by introducing the homogenized wax ester in concentrations that closely mimic the natural tear film. In so doing, significant improvement in the duration of relief offered by ocular lubricants and co-occurring medications is achieved.

It is proposed that the role of wax esters and their hydrolysis products in the tear film maintains the integrity of the interstitial layers themselves, binding the mucin layer to the aqueous layer and aqueous layer to the lipid layer. In addition, the wax esters serve to build up an thicken the mucin, the aqueous layer, and the lipid layer themselves. The binding process and subsequent homeostasis enabled by the wax esters allows the layers of the tear film to cling to each other, thus allowing the entire tear film to remain on the eye for extended periods of time. The ophthalmic composition penetrates all layers of the tear film including the interstitial layers of which no product has incorporated previously. While understanding of this on normal tear films are not fully know or understood internal research has helped us conclude that the glands of the eyelid which include the gland of Krause, gland of Wolfring and gland of Moll excrete wax and wax esters that in combination with the Meibomian gland that excrete lipids and the lachrymal gland aqueous secretions with lip wiper effect of the eyelid due to normal blinking action builds a normal and stable ocular tear film.

The viscosity of the ophthalmic solutions described herein may be measured using techniques well-known to those skilled in the art. Non-limiting examples of methods to measure viscosity include falling ball viscometers, viscosity cups, consistometers (measuring flow on an incline), capillary glass viscometers, or rotational viscometers. A variety of instruments are commercially available (Cole-Palmer Instrument Co., Vernon Hills, Ill., USA).

The extended dwell time on the eye and the shared characteristics with the natural tear film further gives the emulsion the ability to act not only as a lubricant for the eye and ocular prosthesis, but also as an excipient that enables enhanced bioavailability for delivering medications.

This wax-containing emulsion is maintained at a physiological pH between 7.0 and 7.7 so as not to cause discomfort to the patient and will be maintained with a suitable buffering system. The oil phase in a concentration between about 1.0 percent up to about 12.5 percent by weight. Preferably, the oil is present in a range from about 1 percent to about 7.5 percent. In a preferred embodiment, the mineral oil is a mixture of two oils of differing molecular weight.

Formulations for the invention may include combinations of the above ingredients, some of which may necessitate the addition of a preservative that have been recognized by those skilled in the art as safe and acceptable for use on the eye. Examples of preservatives include benzalkonium chloride, PURITE® (Bio-Cide International Inc., Norman, Okla., USA), POLYQUAD® (Alcon Laboratories, Inc., Fort Worth, Tex., USA), GENAQUA® (Novartis Ophthalmics, East Hanover, N.J., USA), Polyhexamthylene biguanide (ICI), OcuPure® (Abbott Laboratories Inc., Chicago, Ill., USA), DISSIPATE® (OCuSOFT, Rosenberg, Tex., USA). See Moshirfar et al., 2014, "Artificial tears potpourri: a literature review" *Clin Ophthalmol.* 8: 1419-1433. In formulations with a preservative, typically ethylene diamine tetraacetate (EDTA) will also be included.

The formulations whether prepared for a sterile multi-dose container or including a preservative may also include a borate buffer. Alternatively, a phosphate buffer may be used.

In a preferred embodiment, the ophthalmic solution is preservative-free. In some embodiments, preservative-free solutions are delivered in single use packages because of the risk of bacterial contamination associated with conventional multi-use applications. In another embodiment, the ophthalmic solution is delivered in a sterile multidose bottle. Several configurations are known. As an example, Aptar Pharma (Crystal Lake, Ill., USA) sells a multidose squeeze dispenser which operates mechanically and utilizes a filter membrane. See PCT Publication Nos. WO 2017/074420 and WO 2017/132190 (Aptargroup, Inc.). This technology is used to deliver a cyclosporin ophthalmic emulsion for the ALLEGAN RESTASIS MULTIDOSE™ product. It is also used to deliver the CLEAR EYES® PURE RELIEF® product. Another sterile multi-use system is the JOT™ product. It is eye drop dispenser that uses pressure to deliver controlled drops and provides a horizontal delivery alternative to current dispensers. http://jotteq.com/about/.

The treatment composition of the invention is an oil-in-water emulsion having an aqueous phase and the wax component containing oil droplets present in each, in addition to a surfactant combination used for the dual purpose of stabilizing the emulsion and spreading the emulsion over the ocular surface following its application to the eye. The surfactant combination may comprise a primary surfactant and secondary surfactant and is one that enables formation of an emulsion that is stable in manufacture and during storage, but desirably meta stable when applied to the ocular surface—i.e., one that rapidly differentiates when applied to the eye whereby a non-blurring film of oil is rapidly formed over the ocular surface and disseminates the wax ester through each phase of the emulsion. A stable emulsion during manufacture and storage is one that may separate into separate phases during standing but can be reconstituted by simple shaking. An unstable emulsion is one that breaks apart typically forming an oil film or slick that cannot be eliminated by simple shaking. In some embodiments, the surfactant is a non-ionic surfactant, such as polysorbate 80, Octoxynol 40 or a diphosphatidylglycerol such as dimyristoylphosphatidylglycerol. In other embodiments, the surfactant is an anionic surfactant. The anionic surfactant may be an anionic polar phospholipid, such as a lysophosphatidylcholine, a phosphatidic acid, a phosphatidylcholine, a phosphatidylethanolamine, a phosphatidylglycerol, or a phosphatidylserine. In a preferred embodiment, the anionic surfactant is a diphosphatidylglycerol. In a preferred embodiment, the surfactant is a mixture of two surfactants.

A meta stable emulsion during use is desirable for purposes of this invention. Though useable for alleviation of dry eye symptoms, a stable emulsion, as opposed to a meta stable emulsion, will not differentiate rapidly when applied to the ocular surface. This is undesirable for the following reasons. An emulsion is typically optically opaque due to the presence of two distinct phases. Therefore, an opaque emulsion over the surface of the eye is likely to cause blurring. The duration of blur is dependent upon the time required for the emulsion to differentiate and form separate layers replicating a tear film. In addition, the emulsion is most easily added to the eye as a standard drop from an eyedropper. The eye is capable of holding a limited volume of fluid of volume that is less than 25 µL. A volume of 25 µL is substantially less than the volume of a standard drop. Therefore, if the emulsion is stable and fails to differentiate rapidly following application to the eye, excess emulsion will be discharged from the eye during blinking. Discharge of the emulsion from the eye will result in discharge of efficacious components of the treatment solution from the eye before a long-lasting tear film can be formed. For this reason, efficacious components may not be available in sufficient quantity to form the desired tear film. Consequently, though a stable emulsion might alleviate the symptoms of dry eye for a limited period of time, it is a lesser preferred embodiment of the invention.

A meta stable emulsion, as the term is used herein, is one that is either stable in storage, or differentiated into two separate layers, but is readily reconstituted by simple shaking prior to use. When a meta stable emulsion is added to the eye as a standard drop, it quickly differentiates permitting rapid formation of an oil film over the corneal surface without excessive oil discharge by blinking. Preferably, the emulsion will differentiate within about 10 blinks following application to the eye, more preferably in a time of less than about 1 minute. Blurring may occur during the time required to move the bulk of the excess liquid to be discharged from the eye. During and following differentiation of the emulsion, the formation of the oil film is assisted by use of the surfactant combination which serves to help form the emulsion and facilitate the spread of the oil over the surface of the eye as the emulsion breaks. Consequently, a meta stable emulsion is the preferred embodiment of this invention.

The emulsions of the invention comprise an oil-in-water emulsion. The oil used to form the emulsion may be derived from animals, plants, nuts, petroleum, etc. Those derived from animals, plant seeds, and nuts are similar to fats and are primarily glycerides or fatty acids and consequently, contain a significant number of acid and/or ester groups rendering the same polar and lesser preferred for purposes of the invention. Examples of these oils are safflower oil, corn oil, canola oil, whale oil and seal oil or chemically similar oils. Alternatively, oils derived from petroleum are usually aliphatic or aromatic hydrocarbons that are essentially free of polar substitution and therefore suitable for purposes of the present invention provided the oil is refined so as to be compatible with human tissue such as the ocular surface. Preferably, the oil is a linear hydrocarbon oil having from 10 to 150 carbon atoms and more preferably, the oil is a saturated n-alkane or isoalkane hydrocarbon having from 10 to 26 carbon atoms. Unsaturated alkene hydrocarbons may be used but are less chemically stable. In a preferred embodiment, the oil is a mixture of two oils of differing molecular weight. In some embodiments mineral oil is the preferred oil for purposes of this invention. Examples of preferred mineral oils are DRAKEOL® 15 and DRAKEOL® 35.

Additional oils that could be used to formulate an appropriate oil in water emulsion may be a vegetable oil such as a castor oil, almond oil, myrcia oil, corn oil, peanut oil, canola oil, safflower oil, kola nut oil, light olive oil, bay leaf oil, or other generally recognized as safe (GRAS) oils listed as being appropriate for ocular formulation. Alternatively, the oil may be one suitable for forming liposomes.

The oil component within the emulsion may vary within reasonable limits provided the amount of oil retained on the eye following its application to the eye is within controlled volumes and does not exceed 25 µL. Preferably, the volume does not exceed 15 µL. More preferably varies between about 1 and 10 µL and most preferably varies between about 1 and 5 µL. If the amount of oil added to the eye is in excess of 15 µL, the oil layer on the surface of the eye may be of excessive thickness and resulting in prolonged blurring. A treatment composition containing the oil in a concentration of at least 0.1 percent by weight of the total composition provides some benefits. A preferred concentration for the oil is at least 1.0 percent of the weight of the treatment composition. Preferably, the oil content of the treatment solution varies between about 1 and 12.5 percent by weight of the composition.

In one preferred embodiment, the beeswax is Cera Alba or Cera Flava. It may be USDA Certified Organic beeswax or convention natural beeswax. Alternatively, it may be a synthetic wax that may be purchased from a variety of sources including Koster Keunen (Watertown, Conn., USA). Such waxes may contain partial hydrolysis products during the preparation of the emulsion.

The quantity of wax used in the formulations described herein may vary. In some embodiments, when the percentage oil tends to the upper portion of the range ~7.5 wt. %, the relative weight percent beeswax will be lower, e.g., 0.5 wt. % or less. Similarly, when the oil tends to the lower portion of its range, the relative weight percent beeswax will be higher 0.75 to 1.25 wt. %.

Other additives may be present in the treatment composition. Such materials include minor amounts of neutral lipids and oils such as one or more triglycerides, partially hydrolyzed esters, cholesterol esters, high molecular weight isoprenoids; stabilizers, additional surfactants; anti-inflammatory compounds; mucomimetics; preservatives; pH adjusters to provide a composition preferably having a pH between about 6.5 and 7.8 and most preferably, between about 7.2 and 7.5; salt, buffer, glycerol, or sugar in sufficient concentration to form a mildly hypotonic composition such that the emulsion is not stable in the ocular environment; etc., all as would be obvious to those skilled in the art.

5.1. Formulations with Medications

Another useful class of additives comprises medications. As a consequence of the long term stability of the oil film formed over the surface of the eye using the emulsion compositions of the invention, prolonged and improved delivery of the medication to the eye results due to increased contact time of the medication on the eye. Medications suitable for delivery to the eye using the film forming compositions of the invention are those soluble in either the aqueous or oil phase of the composition though it is preferable that the medication be soluble in the oil phase. Illustrative medications include antibiotics, antiviral agents, anti-inflammatory agents and antiglaucoma agents such as illustrated in part in published European Patent Application No. 0 092 453 published Oct. 26, 1983, sections 5.3.1 and 5.3.2, or PCT Pub. No. WO 2015/05531 published Apr. 23, 2015, page 5, lines 5-22, incorporated herein by reference.

Some common ophthalmic drugs or active agents suitable for use in this invention include, but are not limited to, adenosine diphosphate ribose, antazoline, apraclonidine, apraclonidine, atropine, azelastine, bepotastine, betaxolol, betaxolol, bimatoprost, brimonidine, brinzolamide, bromfenac, bromfenac, carteolol, cetrimide, chloramphenicol, ciprofloxacin, dexamethasone, diclofenac, dorzolamide, emedastine, epinastine, epinastine, flurbiprofen, framycetin sulphate, gentamycin, gramicidin, hamamelis water, homatropine, hyaluronic acid, ketotifen fumarate, latanoprost, levobunolol, levofloxacin, lodoxamide loteprednol, moxifloxacin, naphazoline, naphazoline, nedocromil maleate, ofloxacin, olopatadine, pegaptanib, pheniramine, pilocarpine, pranoprofen, prednisolone, ranibizumab, rimexolone, sodium, tetracaine, tetrahydrozoline, thiomersal, timolol, tobramycin, trafluprost, travoprost, ketorolac trometamol, trometamol, xylometazoline, and combinations such a travoprost/timolol, dorzolamide/timolol, bimatoprost/timolol, brimonidine/timolol, latanoprost/timolol, brinzolamide/timolol. In a preferred embodiment, the ophthalmic drugs are water or oil phase soluble.

5.2. Preferred Composition Formulation

An example of a preferred formulation is the following in weight percent:

Wax ester: Preferred 0.25% to 1.0% Range: 0.01-1.25%. In some embodiments, the wax ester may be present from 0.25% to 0.35%; 0.30% to 0.40%; 0.35% to 0.45%; 0.40% to 0.50%; 0.45% to 0.55%; 0.50% to 0.60%; 0.55% to 0.65%; 0.60% to 0.70%; 0.65% to 0.75%; 0.70% to 0.80%; 0.75% to 0.85%; 0.80% to 0.90%; 0.85% to 0.95%; 0.90% to 1.00%; 0.95% to 1.05%; 1.00% to 1.10%; 1.05% to 1.15%; 1.10% to 1.20%; or 1.15% to 1.25%. In some embodiments the wax ester may be a beeswax, e.g., a naturally occurring beeswax or a synthetic beeswax.

Oil: Preferred 3.5% to 5.5% using two different weights of oil (e.g., 1.0% DRAKEOL® 15 & 4.5% DRAKEOL® 35). Range: 1.0% to 6.5%. In some embodiments, the oil may be present from 1.0% to 1.5%; 1.25% to 1.75%; 1.5% to 2.0%; 1.75% to 2.25%; 2.0% to 2.5%; 2.25% to 2.75%; 2.5% to 3.0%; 2.75% to 3.25%; 3.0% to 3.5%; 3.25% to 3.75%; 3.5% to 4.0%; 3.75% to 4.25%; 4.0% to 4.5%; 4.25% to 4.75%; 4.5% to 5.0%; 5.75% to 6.25%; or 6.0% to 6.5%.

Polysorbate 80: Preferred 0.4% Range: 0.2% to 0.7%. In some embodiments, the Polysorbate 80 may be present from 0.2% to 0.4%; 0.3% to 0.5%; 0.4% to 0.6%; 0.5% to 0.7%.

In a preferred embodiment, a second surfactant is used, which may be Octoxynol 40 or anionic polar phospholipid (APP). If the second surfactant is Octoxynol 40: Preferred 0.3% Range 0.1% to 0.6%. In some embodiments, the Octoxynol 40 may be present in 0.1% to 0.2%; 0.15% to 0.25%; 0.2% to 0.3%; 0.25% to 0.35%; 0.3% to 0.4%; 0.35% to 0.45%; 0.4% to 0.5%; 0.45% to 0.55%; or 0.5% to 0.6%. If the second surfactant is anionic polar phospholipid (APP), it is preferably a diphosphatidylglycerol such as dimyristoylphosphatidylglycerol: Preferred 0.25%, Range of 0.1% to 0.75%. In some embodiments, the APP may be present in 0.1% to 0.2%; 0.15% to 0.25%; 0.2% to 0.3%; 0.25% to 0.35%; 0.3% to 0.4%; 0.35% to 0.45%; 0.4% to 0.5%; 0.45% to 0.55%; 0.5% to 0.6%; 0.55% to 0.65%; 0.6% to 0.7%; or 0.65% to 0.75%.

Monobasic and Dibasic Phosphate: 0.25% and 0.03% with range of 0.01% to 0.5%.

Sodium Chloride: 0.67% range 0.60% to 0.75%

Formulation pH of 7.6+0.1, −0.6

Osmolality: preferred 230 to 260 mOsmol/kg, range 210 to 260 mOsmol/kg

Deionized Water

Optionally EDTA. If present preferred 0.01%, range 0.007% to 0.02% by weight. Typically, EDTA will be used if there is a preservative in the formulation.

Optionally an anti-inflammatory compound such as deactivated brewer's yeast or adenosine diphosphate ribose, if present preferred 0.02% to 1% by weight.

Optionally, a mucomimetic, such as HP Guar, a glycosylaminoglycan such as hyaluronic acid (HA) or sodium hyaluronate may be included. Typical HA concentrations for an ophthalmic solution range from 0.1% to 0.4%. Other additives such as an emollient or demulcent may be incorporated. Non-limiting examples include polymers of ethylene oxide, propylene oxide, or butylene oxide. Additional examples are carboxymethylcellulose (CMC), hydroxypropyl methylcellulose (HPMC), polyacrylic acid (PAA), polyethylene glycol, (PEG) propylene glycol (PG) or polyvinyl alcohol (PVA). Specific concentrations ranges for liquid polyols: glycerin, 0.2% to 1%; polyethylene glycol 300, 0.2% to 1%; polyethylene glycol 400, 0.2% to 1%; propylene glycol, 0.2% to 1%; or polyvinyl alcohol, 0.1% to 4%. Specific concentrations ranges for cellulose derivatives carboxymethylcellulose sodium, 0.2% to 2.5%; hydroxyethyl cellulose, 0.2% to 2.5%; hydroxypropyl methylcellulose, 0.2% to 2.5%; and methylcellulose, 0.2% to 2.5% See Pucker, A D et al., 2016, "Over the counter (OTC) artificial tear drops for dry eye syndrome", Cochrane Database Syst Rev. February 23; 2:CD009729.

The ophthalmic solutions are brought to the appropriate pH by use of an acid such as HCl or citric acid or a base such as NaOH.

5.3. Definitions

While the following terms are believed to be well understood by one of ordinary skill in the art, the following definitions are set forth to facilitate explanation of the presently disclosed subject matter.

As used herein "wax ester" means a that have long or very long carbon chains and are solids up to 60 or 100° C. They may be natural from animal, vegetal, bacterial sources or synthetic such as beeswax, Chinese wax, Shellac Wax and Spermaceti wax. The preferred wax ester is beeswax, a mixture a wax or wax ester of several components with a typical approximate chemical formula of $C_{15}H_{31}COOC_{30}H_{61}$. For natural beeswax, the primary components are palmitate, palmitoleate, and oleate esters of long-chain aliphatic alcohols, with the ratio of triacontanyl palmitate $CH_3(CH_2)_{29}O$—CO—$(CH_2)_{14}CH_3$ to cerotic acid $CH_3(CH_2)_{24}COOH$, the two principal components, being approximately 6:1. The chemical composition of beeswax is monoesters, 30 to 55%; hydrocarbons, 10 to 18%; free fatty acids, 10 to 15%; di- & complex esters, 8 to 18%; hydroxy monoesters, 3 to 6%; hydroxy polyesters, 7 to 10%; free fatty alcohols, 1 to 2%; minor components 2 to 7%. See Leray, Claude, "Waxes" Kirk-Othmer Encyclopedia of Chemical Technology, Sep. 15, 2016, John Wiley & Sons, vol. 25, pp. 1-25; www.wikipedia.org "Beeswax" accessed Sep. 27, 2018. Natural beeswax is also commercially available as Cera Alba or Cera Flava (White or Yellow Beeswax). Alternatively, the beeswax may be a synthetic beeswax. Typically, a synthetic beeswax is a blend of fatty esters (C32 to C62), high-molecular-weight hydrocarbons (C21 to C34), fatty acids (C16 to C36), and fatty alcohols (C16 to C36). For synthetic beeswax, esters are the most abundant, the hydrocarbons next, the acids, and then the alcohols. Examples of synthetic beeswax may be found in Anderson, U.S. Pat. No. 4,151,001. During the preparation of the emulsion, the wax esters may hydrolyze forming additional acids and/or alcohols as part of the commercial process.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or there below. Alternatively, depending on the context, the term "about" may mean±one half a standard deviation, ±one standard deviation, or ±two standard deviations. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

As used herein, the verb "comprise" as used in this description and in the claims and its conjugations are used in its non-limiting sense to mean that items following the word are included, but items not specifically mentioned are not excluded.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure. All references cited herein are incorporated by reference in their entirety.

5.4. Methodologies to Evaluate the Tear Film

There are a number of methods to diagnose dry eye including patient reported symptoms and ocular tests to evaluate the tear film. Some have expressed concern about the lack of a diagnostic gold standard. See Pucker et al. 2016.

One method is the LIPIVIEW® II Ocular surface interferometer. It is an FDA cleared non-contact diagnostic instrument that measures the lipid layer thickness, blink rates and images the Meibomian gland. TearScience, Morrisville, N.C., USA. See Eom et al., 2013, "Correlation between quantitative measurements of tear film lipid layer thickness and Meibomian gland loss in patients with obstructive Meibomian gland dysfunction and normal controls" Am J Ophthalmol. 155(6) 1104-1110; King-Smith et al., 2010, "Application of a novel interferometric method to investigate the relation between lipid layer thickness and tear film thinning" Invest Ophthalmol Vis Sci. 2010; 51(5): 2418-2423; King-Smith et al., 2009, "The contribution of lipid layer movement to tear film thinning and breakup" Invest Ophthalmol Vis Sci. 2009; 50(6): 2747-2756; Blackie et al., 2009, "The relationship between dry eye symptoms and lipid layer thickness" Cornea 28(7) 789-794. See also Korb et al., U.S. Pat. Nos. 9,545,197; 8,915,592; 8,746,883; and 8,591,033, the contents of which are incorporated herein by reference.

Another method to measure the tear film is the tear breakup time (TBUT). In this test a fluorescein dye is used to stain the eye while the patient does not blink. The time for the tear film to breakup is recorded where >10 seconds is considered normal, 5-10 seconds is marginal and <5 seconds is low. Wang and Craig, 2018, "Comparative Evaluation of Clinical Methods of Tear Film Stability Assessment: A Randomized Crossover Trial" JAMA Ophthalmol. 136(3): 291-294.

5.4.1. Interference Patterns to Evaluate the Tear Film

Figure 1:
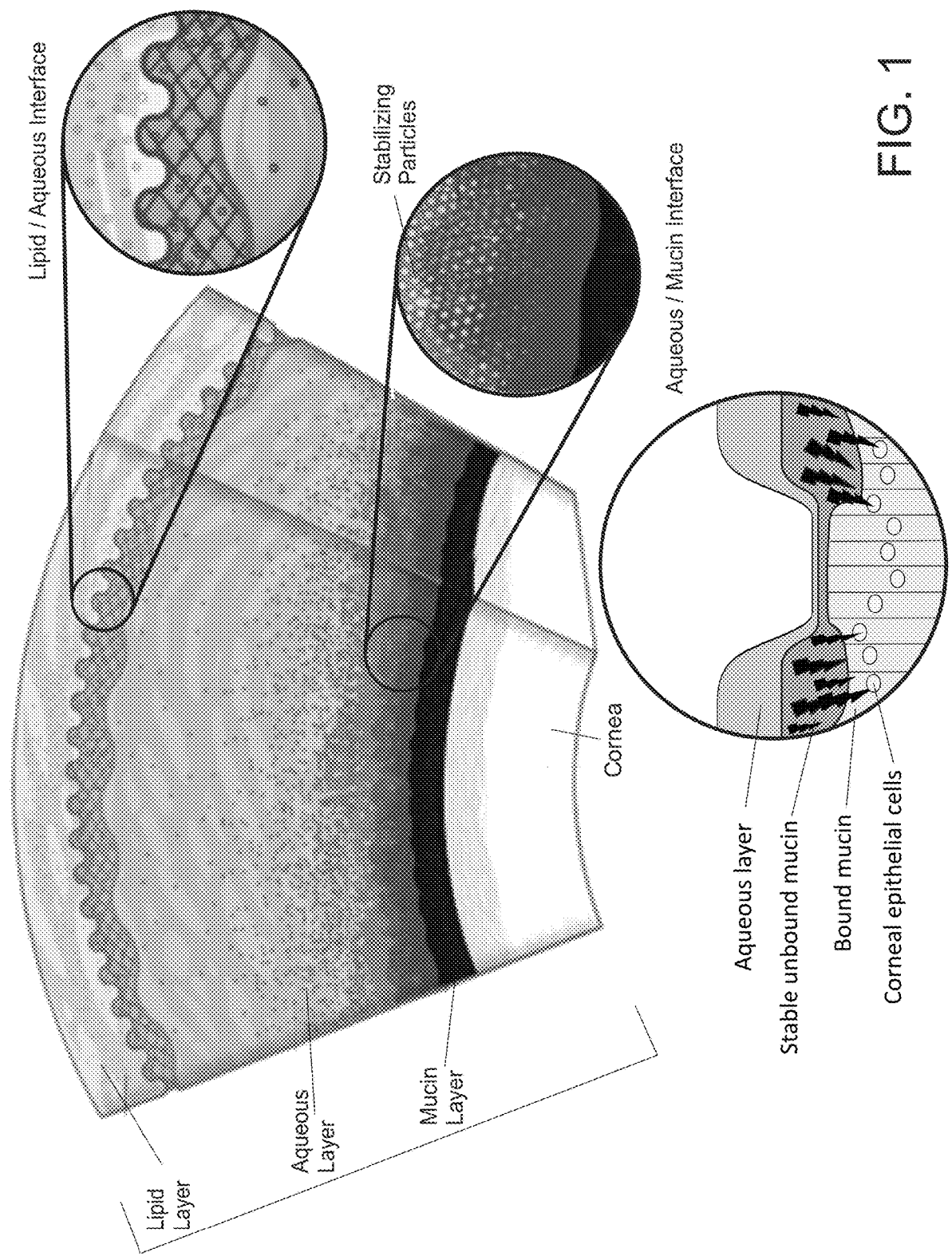

Yet another method to analyze the tear film using light and the observed interference patterns is described below. In this method, a tear film is formed over an ocular surface by either adding one standard drop of treatment solution (40 to 50 μL). Thereafter, the tear film formed is evaluated by projecting a light source onto the ocular surface and viewing the reflected images from the light source on a video screen. The light source and its location are configured to illuminate a surface area on the ocular surface of approximately 10 mm². Interference patterns are formed, the color(s) of which are indicative of the thickness of the oil layer over the ocular surface. The color of the waves is correlated with standards of known film thickness. In this way, tear film is evaluated over a period of real time and first rated in accordance with the following scale. Also see Yokoi et al., 1996, "Correlation of tear lipid layer interference patterns with the diagnosis and severity of dry eye" Am J Ophthalmol 122 818-824. The lipid film thickness determined by the interference patterns in the Film Characteristics column of Table 1 below are known to correlate with the actual lipid film thickness in the tear film. The thickness of the actual lipid film in turn correlates with the overall thickness of the tear film on the eye. See FIG. 1 for the different layers of the tear film.

TABLE 1

| Rating | Film Characteristics | Quality |
|---|---|---|
| A | Colored waves - particularly greens and blues. Waves extend from lower lid to above the lower pupillary border. Film thickness is in excess of 170 nm. | Excellent |
| B | Colored waves - reds, browns, yellows, but no blues. Waves extend from lower lid to above the lower pupillary border. Film thickness of approximately 140 nm. | Very Good |
| C | Colored waves - only yellow is present. Waves extend from lower lid to lower pupillary border. Film thickness of approximately 90 nm. | Good |
| D | Waves visible but no color present or no color other than grayish white. Waves extend from lower lid to lower pupillary border. Film thickness of less than 55 nm. | Fair |
| F | No waves and no color. An absence of any observable tear film movement. Film thickness of less than 25 nm. | Poor |

With respect to the above categories, it should be recognized that because of the extensive degradation of thin films evaluated for the D and F categories, the film thickness is a rough approximation. Having rated the tear film as described above, a numerical format is then utilized to express change in tear film thickness. A numerical grade of 1.0 indicates a change of one letter grade—e.g., if a C baseline finding prior to the application of a drop of treatment composition improved the tear film to a B rating, a numerical grade of 1.0 would be given. A 2.0 numerical grade would indicate a two-letter grade improvement; and a 3.0 numerical grade would indicate a three-letter grade improvement. For many of the following examples: a 3.0 numerical grade represents an improvement from a D to an A, the maximum improvement in accordance with the testing method used because subjects with a grade of F were screened and eliminated from testing. These scales are used in the tables.

In some of the examples, a rating in excess of 3.0 is given. In such instances, the films formed were exceptional and off scale. In most examples, the evaluation of the tear films formed using the treatment composition was over a period of four hours to determine residence time of the film on the eye. Therefore, with time, the numerical rating decreases but in all cases, the numerical rating is based upon the baseline tear film prior to addition of the treatment composition.

The following Examples further illustrate the disclosure and are not intended to limit the scope. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

6. EXAMPLES

6.1. Wax Ester Containing Formulations

This section discusses several primary goals: ophthalmic formulations for improved tear film stability; a controlled, reproducible method for the manufacture of colloidal wax ester particles to be incorporated into the final emulsion at 0.1 to 1.5 wt. % levels, and the formation of a meta-stable emulsion meeting the requirements for over-the-counter (OTC) use.

Readily re-emulsifiable formulations were prepared by replacing the phospholipid 1,2-dimyristoyl-sn-glycero-3-(phospho-rac-(1-glycerol) salt (disodium DMPG) with glyceryl monostearate (GMS), and a reproducible method for the formation of wax particles for addition to these emulsions was established.

6.1.1. Tear Film Stability for Wax Ester Containing Products

In this set of experiments, a wax ester containing oil-in-water emulsion was compared to several other commercially available products.

A beeswax containing ophthalmic solution: H714: 5.0 Dr-21, 10.0% Bee's Milk (Beeswax, Sesame Oil, Lecithin, Methyl Paraben, and Water) (Koster Keunan), 0.18 Tween-80, 0.1 EDTA, and b.a./NaCl to 100 mOsm.

Water soluble polymer solution #1: *DUASORB* (polymeric system containing 0.1% Dextran 70, 0.3% hydroxypropyl methylcellulose 2910), 0.001% polyquaternium-1, sodium borate, KCl, NaCl, $H_2O$, and HCl and/or NaOH.

6.1.2. Water Soluble Polymer Solution #1 vs. Wax Ester for Tear Film Efficacy Tear film performance was evaluated using the standard contralateral eye experiments by observation of the interference patterns as described in Sec. 5.4.1 above.

Method of Delivery

A standard full drop of approximately 50 µL was delivered to the eyes of five subjects.

Results

Figure 2:
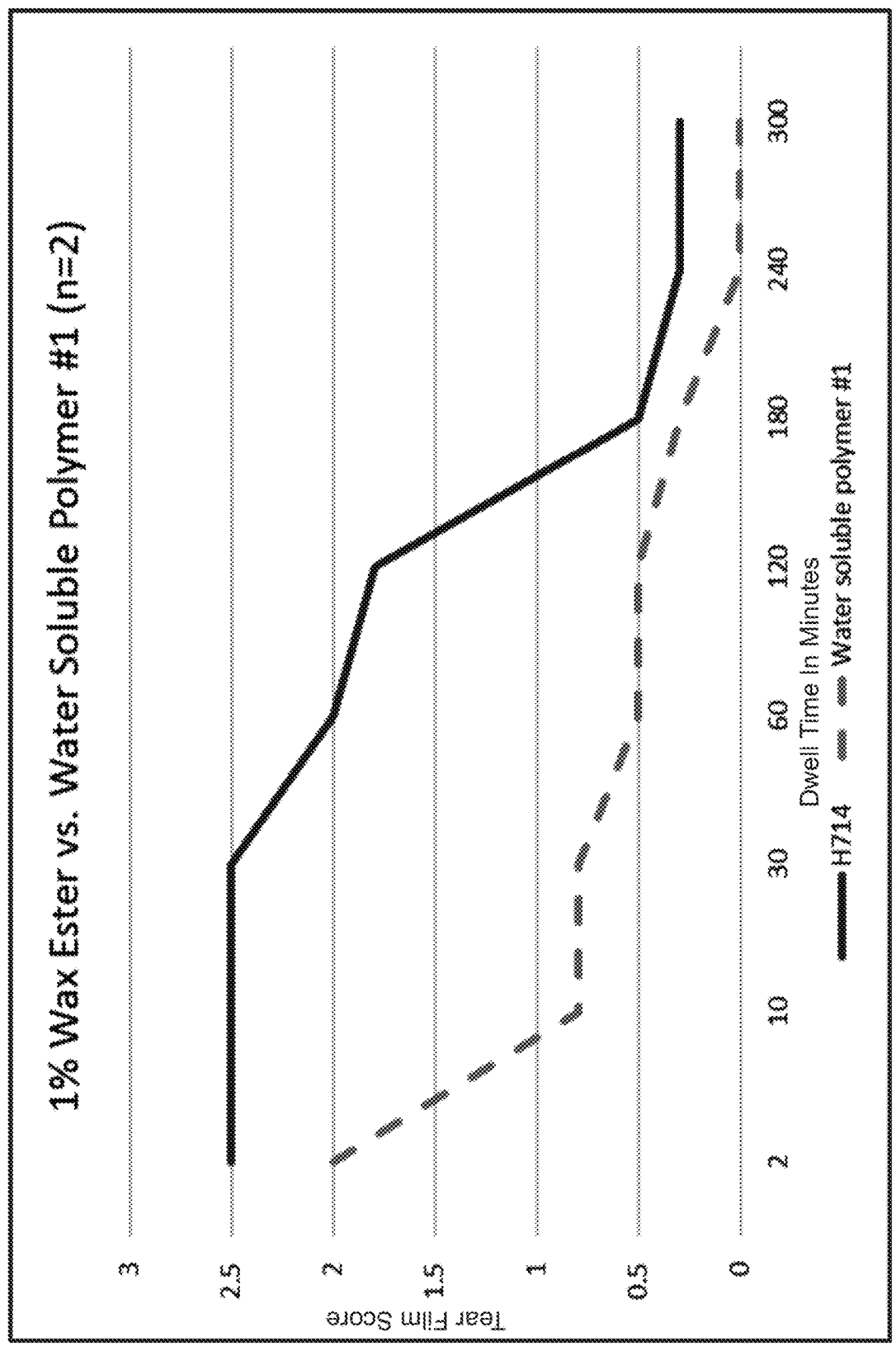
FIG. 2 shows the tear film score over time in minutes (or the dwell time in minutes) for the 1% wax ester prototype product (solid line) vs a commercially available water soluble polymer solutions (dashed line) (n=2).

Wax-ester formulation H714 versus to water soluble polymer solution #1: H714 performed very well in the interference analysis of tear film thickness. Initially, H714 scored 2.5 grades above baseline for the first two hours and returning to baseline after three hours. In one set of experiments the water soluble polymer solution, on the other hand, was 2.0 grades above baseline initially but faded quite rapidly within 30 minutes. In another set of experiments, after instillation both the H714 and the water soluble polymer were at about 1.8 grades above baseline. After 15 minutes water soluble polymer solution #1 went virtually back to baseline, while H714 (~1% beeswax) remained on the eye for over two hours. The water soluble polymer #1 which showed an initial a 2.0 score change showed a return to essentially baseline at 1 hour. (see FIG. 2).

Figure 3:
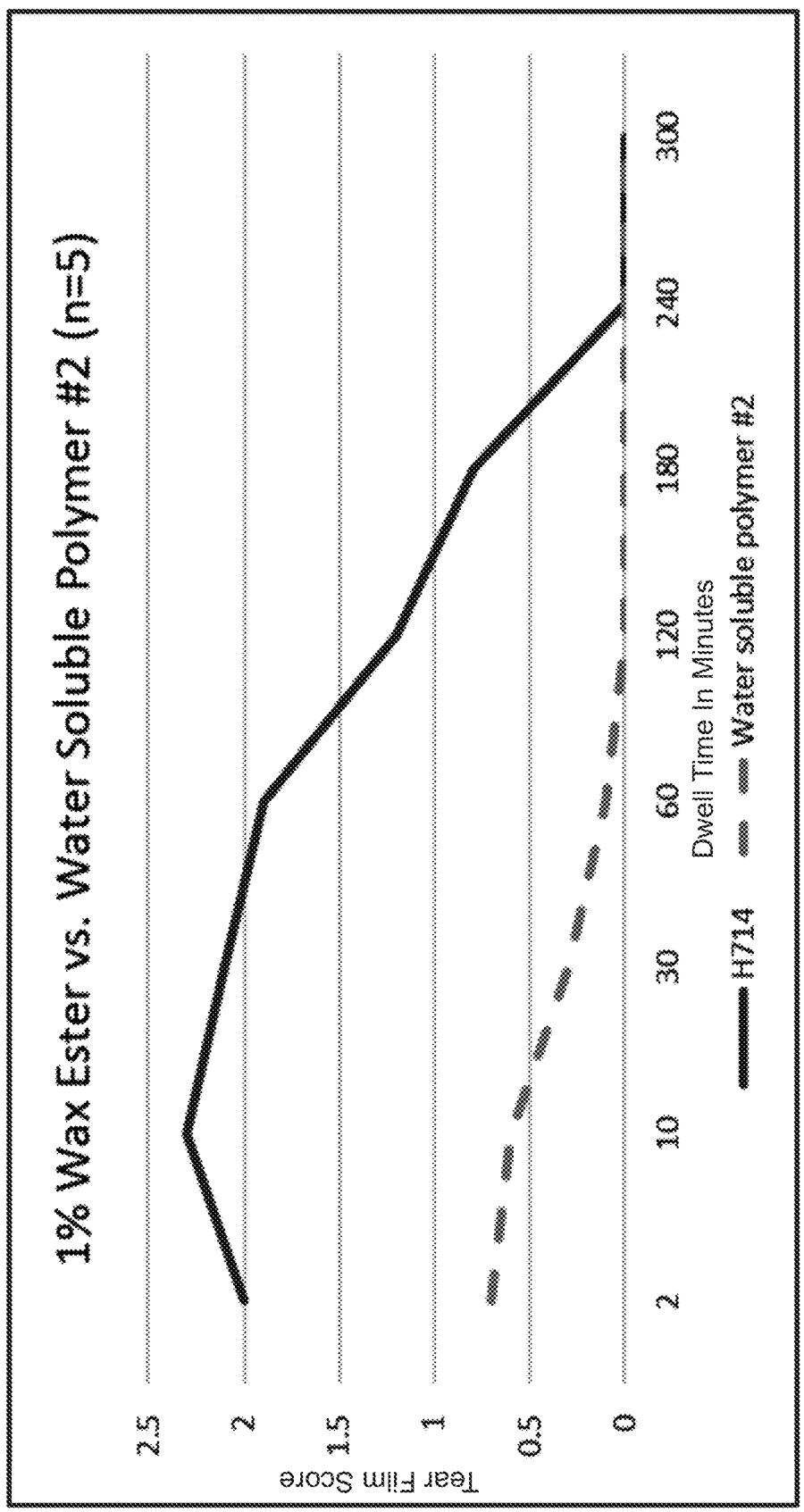
FIG. 3 shows the tear film score over time in minutes (or the dwell time in minutes) for the 1% wax ester prototype product (solid line) vs a commercially available water soluble polymer solutions (dashed line) (n=5).
Figure 4:
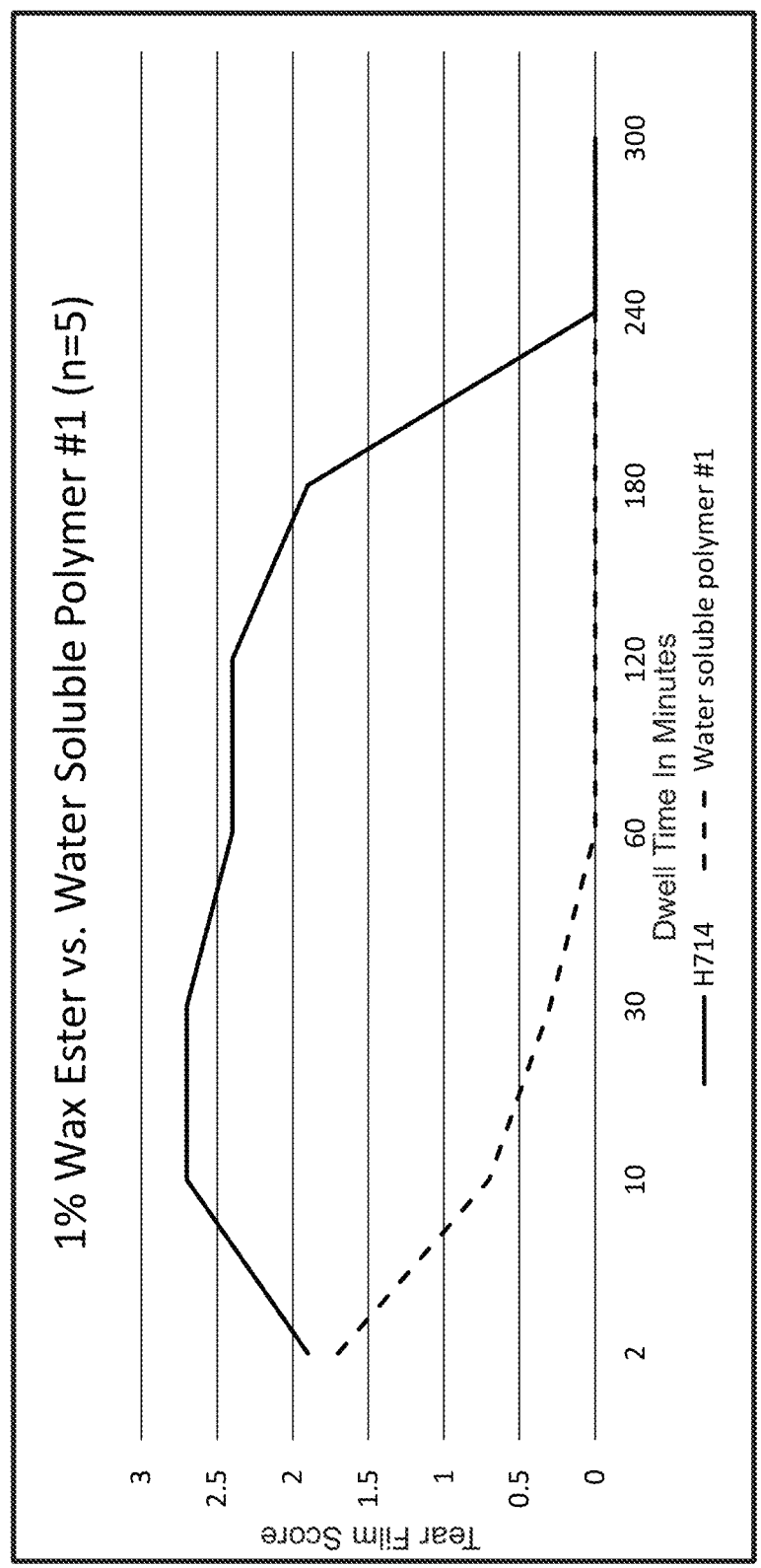
FIG. 4 shows the tear film score over time in minutes (or the dwell time in minutes) for the 1% wax ester prototype product (solid line) vs a commercially available water soluble polymer solutions (dashed line) (n=5).

In another experiment, the H714 formulation was tested versus a second water soluble formulation. The wax ester formulation showed a 2 score increase initially and returned to baseline (less than 0.5 score change) between 3 and 4 hours. The water soluble polymer formula #2 after only showing an approximately 0.7 score change initially, and returned to below 0.5 score change in less than 30 minutes (See FIG. 3). In a third experiment the wax ester formulation was evaluated versus water soluble polymer #1. Initially both formulations showed a score increase of 1.8 grades. The water soluble formula returned essentially to base line in 15 minutes while the wax ester formulation retained its score improvement to beyond 3 hours (see FIG. 4). The results of the tear film analysis for the wax containing formulation, H714 vs. water soluble polymer solution #1 are shown in FIG. 4. The figure shows that the wax ester containing product protects the tear film for significantly longer than the commercially available water soluble polymer solution products. FIG. 5 shows a composite of the results shown in FIG. 3 and FIG. 4. The data demonstrates that the wax ester containing products provide substantially longer duration of protection of the tear film than the other commercially available products. In other words, the wax ester formulations provide durable eye lubrication for greater than 3 hours.

Qualitatively, the second water soluble polymer solutions' appearance was natural throughout the testing period, while H714's appearance ranged from natural to beady to wispy to synthetic, depending on the individual. Within 15 minutes, however, the H714 product yielded natural-looking, colorful, and high-riding waves in all subjects. No blur was reported with either one of the wax ester formulations, but 2/5 of the subjects reported mild sting upon delivery of H714.

6.1.3. Emulsions

The initial research aims were to meet several requirements, including the removal of sodium DMPG (allowing for its replacement by another surfactant) and minimization or elimination of disodium EDTA to increase user comfort. To this end, the disodium EDTA component was excluded from the formulations investigated.

Previous work indicated that sodium DMPG played a crucial role in the creation of the meta-stable emulsion. Thus, a different surfactant may be used to replace the sodium DMPG in order to form a commercially acceptable emulsion.

Initial experiments showed that 'stable' emulsions from mineral oil can be manufactured by optimizing the hydrophile-lipophile-balance (HLB) level of a surfactant mixture of SPAN-80® and polysorbate-80, along with the optimization of concentration and processing parameters (temperature, homogenization). The product was a 'stable' emulsion from a chemical degradation point of view but not necessarily from a colloidal kinetic point of view. In fact, it is desired that the emulsion be metastable with respect to phase separation.

In studies described below, the emulsion formulation was used as the model system in which we replaced components as necessary to meet commercial requirements.

6.1.4. Emulsions without Phospholipid (Replacement of DMPG Sodium with GMS)

Emulsions were prepared by replacing the Na-DMPG by GMS at surfactant concentrations of 0.15 and 0.30 wt. % based on total composition. (In these experiments, disodium EDTA was not added to the formulation). The ratio of Myrj-52 and GMS was varied to adjust the calculated HLB of the surfactant mixture. The emulsified phase consisted of ~5.0 wt. % Drakeol-35 mineral oil. The sample compositions are listed in Table 2. The aqueous phase contained 0.67 g NaCl and 0.05 g of $Na_2HPO_4$ (anhydrous) per 100 ml of the water phase.

TABLE 2

Sample compositions and calculated HLB values for emulsions without DMPG sodium

|    | HLB  | g Myrj-52 | g GMS | g Drakeol 35 | Surfactant Content |
|----|------|-----------|-------|--------------|--------------------|
| 1  | 11.1 | 0.094     | 0.065 | 5.700        | 0.15%              |
| 2  | 12.0 | 0.102     | 0.054 | 5.334        | 0.15%              |
| 3  | 13.0 | 0.112     | 0.042 | 5.508        | 0.15%              |
| 4  | 13.7 | 0.127     | 0.037 | 5.404        | 0.15%              |
| 11 | 14.2 | 0.130     | 0.030 | 5.284        | 0.15%              |
| 12 | 15.1 | 0.139     | 0.020 | 5.284        | 0.15%              |
| 13 |      |           |       |              |                    |
| 14 | 16.1 | 0.298     | 0.017 | 5.309        | 0.30%              |
| 15 | 15.0 | 0.279     | 0.042 | 5.300        | 0.30%              |
| 16 | 14.0 | 0.258     | 0.065 | 5.283        | 0.30%              |
| 17 | 12.9 | 0.233     | 0.091 | 5.308        | 0.31%              |
| 18 | 12.0 | 0.207     | 0.108 | 5.303        | 0.30%              |

The described conditions produced emulsions which were readily re-emulsified after phase separation. In general, an increasing value of the calculated HLB lead to a more complete phase separation on standing, as indicated by a decrease in the turbidity of the aqueous phase. After an extended period, some of the oil in the formulations shown in Table 2 did not remain in the dispersed state.

Since the compositions listed in Table 2 appear promising, further investigations were performed to determine the effects of increased surfactant concentrations, 0.1 wt. % of disodium EDTA, and a light mineral oil added to the formulation.

6.1.5. Emulsions with Wax Esters (Particles Dispersed in Aqueous Phase)

Emulsion and dispersed beeswax particle blends were prepared by the addition of beeswax particle dispersions (in high ionic strength media) to previously prepared emulsions with the compositions shown in Table 2. The resulting beeswax (BW) concentrations in the blends are shown in Table 3.

TABLE 3

Emulsion beeswax loading after blending emulsions with wax ester particle dispersions.

| HLB   | BW content | Surfactant content |
|-------|------------|--------------------|
| 11.05 | 0.11%      | 0.13%              |
| 11.99 | 0.11%      | 0.12%              |
| 13.03 | 0.10%      | 0.12%              |
| 13.70 | 0.10%      | 0.13%              |
| 15.11 | 0.09%      | 0.13%              |
| 16.13 | 0.09%      | 0.26%              |
| 15.04 | 0.09%      | 0.26%              |
| 14.04 | 0.09%      | 0.26%              |
| 12.91 | 0.10%      | 0.26%              |
| 12.03 | 0.09%      | 0.26%              |

It was found that BW particles dispersed in an aqueous phase which was similar in composition to the continuous phase of the emulsion could be blended with the emulsions successfully without aggregation of the BW particles.

6.2. Wax Ester Containing Emulsions and Autoclaving

Because of the limitations of many of the existing products for dry eye various methods for the preparation of the second-generation product were investigated. An example was prepared by a co-emulsification technique. Although this was a clinically viable product as mentioned above, this sample did not exhibit adequate commercial stability characteristics.

In general, it was noted that the ocular emulsions, which showed good clinical results and adequate stability in the autoclave, fail when autoclaved with added wax esters such as those disclosed above. In a typical experiment, the failure consisted of gross wax aggregation with an exclusion of the wax ester as a separate phase: the beeswax particles do not remain dispersed after the autoclaving is completed. If aggregation occurs the concentrations delivered to the eye become erratic and the wax particles may irritate the eye.

In order to establish the cause of this failure, the behavior of emulsions and beeswax particle dispersions were investigated separately, with the eventual goal of forming an appropriate blend for clinical testing. This work lead to a method to manufacture a wax ester containing 'second generation' ocular emulsion with improved stability and performance.

Research indicated that the method used for producing a product will need to be modified to successfully make a wax ester containing emulsion that is also shelf stable. The modified procedure consists of the separate preparation and autoclaving of the wax ester particle dispersion and emulsion components, followed by an aseptic blending step to ensure product sterility. The different steps are described separately below.

6.2.1. Wax Ester Emulsion Component Processing

Since it was not possible to create with a single autoclaving step the final wax ester containing emulsion product, a two-step preparation method was developed, with a final sterile blending step, which combined the components. This was done to prevent the chemistry of the emulsion from influencing the stability of the wax ester particles under autoclave conditions.

Due to the mutual dilution effect, which occurs during blending, the emulsion component was prepared as described above, but with concentrations of all the contents doubled with respect to water. The increased concentration of the emulsified oil mixture affected the behavior of the emulsions in the autoclave, where increased loading (amounts of the dispersed emulsion components) eventually lead to emulsion failure during autoclaving. FIG. 6 shows an overlay of the particle size distributions obtained from 2× (solid line), 3× (dashed line), and 4× (open circles) concentrated emulsions before (top panel) and after (bottom panel) autoclaving.

FIG. 6 shows that doubly or triply concentrated beeswax emulsion samples with adequate autoclave stability can be prepared and then diluted with stable wax ester dispersions to attain a desired wax ester concentration in the samples. The primary result of these findings is that a production method can be defined where the emulsions are prepared in concentrated form, autoclaved, and then aseptically blended in a final packaging step with a previously autoclaved wax particle dispersion. The consequences of the autoclaving are a concomitant concentration dependent increase in the mean size of the particle size distribution-resulting in increased meta-stability.

The final blending step (with the wax ester dispersion described below) dilutes the emulsion components back to the desired final concentrations and supplies the wax particles for the 'second generation' ocular emulsion. This step also provides a method for 'fine-tuning' the relative concentrations of wax ester and mineral oil to provide for optimum clinical performance.

6.2.2. Formulation of Wax Ester Particle Dispersions

The wax particle dispersions were prepared by homogenization of melted beeswax (~1.0%) in distilled water with added Octoxynol-40 (~0.2%) at ~75° C. for example. The high cloud point of octoxynol-40 (>100° C.) means that it's emulsifying efficiency increases at higher temperatures by a decrease in its water solubility (effective lowering of the HLB value). Therefore, under autoclave conditions, it is expected that Octoxynol-40 will stabilize the melted wax droplets by re-partitioning from the dissolved state in the aqueous phase onto the particle/droplet surfaces and preventing flocculation.

Since the melting point of beeswax is ~63° C., it is completely melted under autoclave conditions, and the dispersion consists of beeswax droplets in water and surfactant. As the sample temperature continuously increases during the autoclaving process, the Octoxynol-40 becomes increasingly insoluble in water, and tends to migrate towards the particle surface (droplet/aqueous interface) helping to stabilize the melted beeswax droplet. However, at the low surfactant concentrations utilized in these experiments, this mechanism alone may not provide sufficient stabilization for these particles/droplets.

Previous experiments showed that sub-micron beeswax particles in water are highly negatively charged (high negative value of the zeta potential), and the resulting electrostatic repulsion is a substantial contribution to their stabilization. In fact, the sub-micron sized particles can be autoclaved with only a small change in their particle size distribution. However, there is no surfactant present in these dispersions. This fact demonstrates the importance of the electrostatic repulsion model as a stabilization mechanism, even in the absence of a surfactant.

The size distributions of the sub-micron sized particles before (black line) and after (red line) autoclaving are shown in FIG. 7. However, due to complicated processing, the sub-micron sized particles are not expected to be useful in a commercial product for dry eye with long-lasting effects.

The large sized particle dispersions cannot be prepared in the absence of added surfactant. The operating particle formation mechanism is different from a simple nucleation and particle growth model used in the formation of submicron sized dispersions. In this case, an emulsification technique is used, where the added surfactant stabilizes the growing beeswax droplets during the homogenization sequence. The surfactant is also important in preventing droplet aggregation during the cooling period after autoclaving.

In addition to chemical considerations, processing methods assume a critical role: the success or failure in the autoclaving of these particles is completely dependent on the method used. The chemistry of the system yields particle dispersions that are stable in the autoclave (as melted beeswax droplets), but which aggregate irreversibly once the decreasing sample temperature during sample cooling approaches the melting point (crystallization temperature) of the beeswax.

Although the zeta potential values cannot be measured under autoclave conditions, it is visually observed that sealed beeswax particles/droplets dispersions remain stable at 121° C. (with gentle stirring) when dispersed in water.

FIG. 8 shows typical particle size distributions of the wax ester particles in water and Octoxynol-40 (obtained by the emulsification process) before and after autoclaving.

In view of the importance of the wax particle charge in its stability, the salt content also becomes an essential parameter. That is, at high ionic strength (salt concentration) the particles tend to aggregate, which in the case of soft wax results in irreversible coalescence under autoclave conditions (even in the presence of some surfactant). The consequence of this finding is that the beeswax particles cannot be autoclaved in an aqueous phase, which contains large salt concentrations (high ionic strength systems).

6.2.3. Emulsion Blending

The blending step (concentrated emulsions and beeswax dispersions) ensures that proper amounts can be combined to achieve the desired final concentrations of mineral oil, beeswax, and other components in the submitted product. This procedure also allows variation of the total beeswax content in the final product, while maintaining a constant emulsion component composition. Essentially, in this procedure, the emulsion is formulated with increased component levels, while the beeswax particles are emulsified in distilled water with an added surfactant. The concentrations of the various components in the two fractions (before autoclaving) can be tailored to permit a relatively wide variation of final emulsion compositions.

The mechanism involved in the irreversible aggregation of the wax (wax breakout) under autoclave conditions appears to involve the presence of relatively high (approximately isotonic) salt concentrations. This high ionic loading serves to significantly decrease the zeta-potential of the wax ester particles, which essentially removes an important stabilization mechanism when these dispersions are subjected to autoclave conditions. The presence of the Octoxynol-40 helps stabilize the beeswax emulsions at the high temperatures present in the autoclave.

Laser diffraction analysis shows that the emulsions are not subjected to significant amounts of particle aggregation when prepared in this fashion. This is the primary reason why the blended emulsions are expected to show good long-term stability characteristics.

Both components were then autoclaved separately and mixed in equal proportions (by mass) to yield the final product containing either 0.5 wt. % or 1.0 wt. % wax ester.

7. GENERALIZED STATEMENTS OF THE DISCLOSURE

The following numbered statements provide a general description of the disclosure and are not intended to limit the appended claims.

Statement 1: This disclosure provides an ophthalmic solution which comprises an oil-in-water emulsion comprising water; an oil; a surfactant; a present in a concentration of about 0.1 to about 1.5 weight percent; and wherein the ophthalmic solution (i) forms a meta stable emulsion which separates into an oil phase and a water phase on contact with an eye; and (ii) provides lubrication for about 2 to about 12 hours on the eye. The ophthalmic solution provides a stable and appropriately normal tear film thickness that can be demonstrated by interferometry or Tear Film Breakup Time (TBUT) or other methods of diagnosis.

Statement 2: This disclosure provides the ophthalmic solution of Statement 1, wherein on contact with an eye interacts with: (iii) a lipid layer; (iv) an aqueous layer; (v) a mucin layer; (vi) an interface between the lipid layer and the aqueous layer; and (vii) an interface between the aqueous layer and the mucin layer of the eye and/or the corneal cells.

Statement 3: This disclosure provides the ophthalmic solution of any of Statements 1-2, wherein the wax ester is a natural or a synthetic beeswax such as Cera Alba or Cera Flava.

Statement 4: This disclosure provides the ophthalmic solution of any of Statements 1-3, wherein the wax ester is present in a concentration of about 0.1 to about 1.25 weight percent.

Statement 5: This disclosure provides the ophthalmic solution of any of Statements 1-4, wherein the oil is a mixture of a lighter molecular weight oil and a heavier molecular weight oil.

Statement 6: This disclosure provides the ophthalmic solution of any of Statements 1-5, wherein the mineral oil is present in a concentration of about 1.0 to about 7.5 weight percent.

Statement 7. The ophthalmic solution of Statement 6, wherein the oil is a mineral oil.

Statement 8. The ophthalmic solution of Statement 6, wherein the oil is a vegetable oil.

Statement 9 The ophthalmic solution of any Statements 1-8, wherein the surfactant comprises a phospholipid.

Statement 10. The ophthalmic solution of any of Statements 1-9, wherein the surfactant comprises a non-ionic surfactant.

Statement 11. The ophthalmic solution of any of Statements 1-10, wherein the surfactant is a mixture of two or more surfactants.

Statement 12. The ophthalmic solution of Statement 10, wherein the mixture of two or more surfactants comprises a Polysorbate 80, an Octoxynol 40 or an anionic polar phospholipid (APP).

Statement 13, The ophthalmic solution of Statement 1, wherein (i) the oil is a mixture of a lighter molecular weight and a heavier molecular weight oil and is present in a concentration of about 1 to about 5.5 weight percent; (ii) the surfactant mixture of a Polysorbate 80 in a concentration of about 0.35 to about 0.45 weight percent and a dimyristoylphosphatidylglyerol in a concentration of about 0.3 to about 0.4 weight percent; (iii) the beeswax is Cera Alba or Cera Flava in a concentration of about 0.25 to about 1.0 weight percent; and the ophthalmic solution has an osmolality of about 230 to about 260 mOsmol/kg.

Statement 14. The ophthalmic solution of any of Statements 1-13, further comprising a medication.

Statement 15. The ophthalmic solution of any of Statements 1-14, packaged in a sterile multi-use or single use container.

Statement 16. The ophthalmic solution of any of Statements 1-15, packaged in a multi-dose non-preserved (MDNP) container.

Statement 17, The ophthalmic solution of any of Statements 1-14, further comprising a preservative such as stabilized oxychloro complex (PURITE®) or polyhexamethylene biguanide (PHMB) or Polyquaterium-1 (Alcon).

Statement 18. The ophthalmic solution of any of Statements 1-14, for use as a rewetting and/or lubricating solution for an ocular prosthesis.

Statement 19. An ophthalmic solution which comprises an oil-in-water emulsion comprising water; an oil; a surfactant; a beeswax comprising wax esters and partially hydrolyzed ester; wherein wax esters and partially hydrolyzed esters in the ophthalmic solution binding a mucin layer, an aqueous layer, and a lipid layer in an eye of a subject and act to maintain the integrity of an interstitial layer between the mucin layer and the aqueous layer, an interstitial layer between the aqueous layer and the lipid layer.

Statement 20 The ophthalmic solution of Statement 18, wherein the wax esters act to increase the thickness of the mucin layer, the aqueous layer, or the lipid layer.

Statement 21. The ophthalmic solution of Statement 19, wherein the wax esters act to augment the mucin layer, the aqueous layer, and the lipid layer.

Statement 22. The ophthalmic solution of any of Statements 19-21, wherein the binding and homeostasis enabled by the wax esters allows the mucin layer, the aqueous layer and the lipid layer of a tear film to interact with to each other allowing the tear film to remain on the eye for extended periods of time.

Statement 23. A method for delivering a medication or active agent to a subject which comprises administering to an eye of the subject an ophthalmic solution which comprises a medication and an oil-in-water emulsion comprising water; an oil; a surfactant; a beeswax; and wherein the ophthalmic solution (i) forms a meta stable emulsion which separates into an oil phase and a water phase on contact with an eye; and (ii) provides lubrication for about 2 to about 12 hours on the eye.

Statement 24. The method of Statement 23, wherein the medication is a water soluble medication.

Statement 25. The method of Statement 23, wherein the medication is an oil soluble medication.

Statement 26. A method for alleviating the symptoms of dry eye which comprises contacting an eye with an ophthalmic solution comprising an oil-in-water emulsion which emulsion comprises: water; an oil; a surfactant; a beeswax or wax ester combination; and wherein the ophthalmic solution (i) forms a meta stable emulsion which separates into an oil phase and a water phase on contact with an eye; and (ii) provides lubrication for about 2 to about 12 hours on the eye.

Statement 27. The method of Statement 26 wherein on contact with an eye the ophthalmic solution interacts with: (iii) a lipid layer; (iv) an aqueous layer; (v) a mucin layer; (vi) an interface between the lipid layer and the aqueous layer; and (vii) an interface between the aqueous layer and the mucin layer of the eye.

Statement 28. The method of any of Statements 26-27, wherein the beeswax is Cera Alba or Cera Flava.

Statement 29. The method of any of Statements 26-28 wherein the oil is a mixture of a lighter molecular weight oil and a heavier molecular weight oil.

Statement 30. The method of any of Statements 26-29, wherein the oil is present in a concentration of about 1.0 to about 7.5 weight percent.

Statement 31. The method of Statement 30, wherein the oil is a mineral oil.

Statement 32. The method of Statement 30, wherein the oil is a vegetable oil.

Statement 33. The method of any of Statements 26-30, wherein the surfactant is a mixture of two or more surfactants.

Statement 34. The method of any of Statements 26, wherein (i) the oil is a mixture of a lighter molecular weight oil and a heavier molecular weight oil and is present in a concentration of about 1.0 to about 5.5 weight percent; (ii) the surfactant is a mixture of a Polysorbate 80 in a concentration of about 0.35 to about 0.45 weight percent and a dimyristoylphosphatidylglyerol in a concentration of about 0.3 to about 0.4 weight percent; (iii) the beeswax is Cera Alba or Cera Flava in a concentration of about 0.25 to about 1.0 weight percent; and the ophthalmic solution has an osmolality of about 230 to about 260 mOsmol/kg.

Statement 35. The method of any of Statements 26, wherein (i) the oil is a mixture of a lighter molecular weight oil and a heavier molecular weight oil and is present in a concentration of about 1.0 to about 5.5 weight percent; (ii) the surfactant is a mixture of a Polysorbate 80 in a concentration of about 0.35 to about 0.45 weight percent and a dimyristoylphosphatidylglyerol in a concentration of about 0.3 to about 0.4 weight percent; (iii) the artificial beeswax, a combination of wax esters and partially hydrolyzed wax esters in a concentration of about 0.25 to about 1.0 weight percent; and the ophthalmic solution has an osmolality of about 230 to about 260 mOsmol/kg.

Statement 35. The method of any of Statements 26-35, wherein the ophthalmic solution is packaged in a sterile multi-use or sterile single use container.

Statement 36. The method of any of Statements 25-35, wherein the ophthalmic solution is packaged in a multi-dose non-preserved (MDNP) container.

Statement 37. A method of preparing an ophthalmic solution providing lubrication for about 2 to about 12 hours on the eye, wherein the solution is a meta stable oil-in-water emulsion, wherein the method comprises: preparation of a wax dispersion comprising a beeswax or artificial beeswax and a surfactant in a deionized water solution; preparation of an oil-in-water emulsion comprising an oil in a deionized water solution; separately autoclaving the beeswax dispersion and the oil-in-water emulsion; and aseptically blending the autoclaved beeswax dispersion and the oil in water emulsion so as to prepare the meta stable oil-in-water emulsion ophthalmic solution which provides lubrication for about 2 to about 12 hours on the eye.

Statement 38. The method of Statement 37, wherein on contact with an eye the ophthalmic solution penetrates: (iii) a lipid layer; (iv) an aqueous layer; (v) a mucin layer; (vi) an interface between the lipid layer and the aqueous layer; and (vii) an interface between the aqueous layer and the mucin layer of the eye.

Statement 39. The method of any of Statements 37-38, wherein the beeswax is Cera Alba or Cera Flava.

Statement 40. The method of any of statements 37-38, wherein the wax is an artificial beeswax Statement 41. The method of any of Statements 37-40, wherein the oil is a mixture of a lighter molecular weight oil and a heavier molecular weight oil.

Statement 42. The method of any of Statements 37-40, wherein the surfactant is a mixture of two or more surfactants.

Statement 41. The method of Statement 37, wherein (i) the oil is a mixture of a lighter molecular weight oil and a heavier molecular weight oil and is present in a concentration of about 1.0 to about 5.5 weight percent; (ii) the surfactant is a mixture of a Polysorbate 80 in a concentration of about 0.35 to about 0.45 weight percent and a dimyristoylphosphatidylglyerol in a concentration of about 0.3 to about 0.4 weight percent; (iii) the beeswax is Cera Alba or Cera Flava in a concentration of about 0.25 to about 1.0 weight percent; and the ophthalmic solution has an osmolality of about 230 to about 260 mOsmol/kg.

Statement 43. The method of any of Statements 37-42, wherein the ophthalmic solution is packaged in a sterile multi-use or sterile single use container.

Statement 44. The method of any of Statements 37-42, wherein the ophthalmic solution is packaged in a multi-dose non-preserved (MDNP) container.

Statement 45 A method of preparing an ophthalmic solution which comprises an oil-in-water emulsion comprising water; an oil; a surfactant; beeswax or artificial beeswax comprising wax esters; wherein wax esters or hydrolysis products in the ophthalmic solution bind to a mucin layer, an aqueous layer, and a lipid layer in an eye of a subject and act to maintain the integrity of an interstitial layer between the mucin layer and the aqueous layer, and an interstitial layer between the aqueous layer and the lipid layer.

Statement 46. The method of Statement 45, wherein the wax esters or hydrolysis products act to increase the thickness of the mucin layer, the aqueous layer, or the lipid layer.

Statement 47. The method of any of Statements 45-46, wherein the wax esters act to increase the thickness of the mucin layer, the aqueous layer, and the lipid layer.

Statement 48. The method of any of Statements 45-46, wherein the binding and homeostasis enabled by the wax esters or hydrolysis products allows the mucin layer, the aqueous layer and the lipid layer of a tear film to interact with to each other allowing the tear film to remain stable on the eye for extended periods of time.

Statement 49. A method for delivering a medication to a subject which comprises administering to an eye of the subject an ophthalmic solution which comprises a medication and an oil-in-water emulsion comprising: (a) water; (b) an oil; (c) a surfactant; (d) a beeswax; and (e) wherein the ophthalmic solution (i) forms a meta stable emulsion which separates into an oil phase and a water phase on contact with an eye; and (ii) provides lubrication for about 2 to about 12 hours on the eye by providing a stable and appropriately normal tear film thickness that can be demonstrated by interferometry or Tear Film Breakup Time (TBUT) or other methods of diagnosis.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world. It is to be understood that, while the disclosure has been described in conjunction with the detailed description, thereof, the foregoing description is intended to illustrate and not limit the scope. Other aspects, advantages, and modifications are within the scope of the claims set forth below. All publications, patents, and patent applications cited in this specification are herein incorporated by reference as if each individual publication or patent application were specifically and individually indicated to be incorporated by reference.

What is claimed is:

1. An ophthalmic solution consisting of:
a wax dispersion comprising natural beeswax particles, an anionic polar surfactant and water;
sodium hyaluronate; and
an oil-in-water emulsion comprising an oil and water; and
optionally, at least one preservative selected from the group consisting of polyhexamethylene biguanide, stabilized oxychloro complex and polyquaternium-1,
wherein:
(i) the oil is a mixture of a lighter molecular weight mineral oil and a heavier molecular weight mineral oil and is present in a concentration of about 4.0 to about 6.25 weight percent;
(ii) the anionic polar surfactant is a mixture of a Polysorbate 80 in a concentration of about 0.35 to about 0.45 weight percent and an anionic polar dimyristoylphosphatidylglycerol in a concentration of about 0.35 to about 0.50 weight percent; and
(iii) the natural beeswax particles are solid up to about 60° C. and are present in a concentration of about 0.50 to about 1.25 weight percent; and
wherein the ophthalmic solution:
(i) forms a meta stable emulsion which separates into an oil phase and a water phase on contact with an eye;
(ii) provides a dwell time on the eye of at least two hours;
(iii) is formulated as a free flowing liquid at room temperature;
(iv) has an osmolality of about 230 mOsmol/kg to about 260 mOsmol/kg; and
(v) has a pH of from about 6.5 to about 7.8.

2. The ophthalmic solution of claim 1, wherein on contact with an eye penetrates:
a lipid layer;
an aqueous layer;
a mucin layer;
an interface between the lipid layer and the aqueous layer; and
an interface between the aqueous layer and the mucin layer of the eye and or the corneal cells.

3. The ophthalmic solution of claim 1, wherein the beeswax is present in a concentration of about 1.0 weight percent.

4. The ophthalmic solution of claim 1, wherein the beeswax is Cera Alba or Cera Flava.

5. The ophthalmic solution of claim 1, packaged in a sterile single use container.

6. The ophthalmic solution of claim 1, packaged in a sterile multi-dose container.

7. The ophthalmic solution of claim 1, for use as a rewetting and/or lubricating solution for an ocular prosthesis.

* * * * *